(12) United States Patent
Feinstein et al.

(10) Patent No.: US 12,077,812 B2
(45) Date of Patent: Sep. 3, 2024

(54) COMPOSITIONS AND METHODS USEFUL IN DETECTING AND DIAGNOSING MULTIPLE SCLEROSIS

(71) Applicants: The United States Government As Represented By The Department of Veterans Affairs, Washington, DC (US); THE BOARD OF TRUSTEES OF THE UNIVERSITY OF ILLINOIS, Urbana, IL (US)

(72) Inventors: Douglas Feinstein, Chicago, IL (US); Anne Boullerne, Chicago, IL (US)

(73) Assignees: The United States Government As Represented By The Department Of Veterans Affairs, Washington, DC (US); The Board Of Trustees Of The University Of Illinois, Urbana, IL (US)

( * ) Notice: Subject to any disclaimer, the term of this patent is extended or adjusted under 35 U.S.C. 154(b) by 0 days.

(21) Appl. No.: 17/715,187

(22) Filed: Apr. 7, 2022

(65) Prior Publication Data
US 2022/0333159 A1   Oct. 20, 2022

Related U.S. Application Data

(60) Provisional application No. 63/171,789, filed on Apr. 7, 2021.

(51) Int. Cl.
*C12Q 1/686* (2018.01)
(52) U.S. Cl.
CPC ....... *C12Q 1/686* (2013.01); *G01N 2800/285* (2013.01)

(58) Field of Classification Search
None
See application file for complete search history.

(56) References Cited

U.S. PATENT DOCUMENTS

2018/0245138 A1 * 8/2018 Yamamura ........... A61K 35/744

FOREIGN PATENT DOCUMENTS

WO   WO-2019012137 A1 *  1/2019
WO   WO-2021039932 A1 *  3/2021

OTHER PUBLICATIONS

Boullerne et al., J. Neuroimmunol., 343(577237): 1-6 (2020) (Year: 2020).*
Shahi et al., Gut Microbes, 8(6):607-615 (2017) (Year: 2017).*
Chen et al., J. Autoimmunity, 83:31-42 (2017) (Year: 2017).*
Sorini et al., Front. Immunol., 9(2667):1-10 (2018) (Year: 2018).*
Chopra et al., J. Mol. Sci, 22:1-18 (2021) (Year: 2021).*
Freedman et al., Neurotherap., 15:109-125 (2018) (Year: 2018).*
Jangi et al., Nature Comm., 7(12015):1-11 (2016) (Year: 2016).*
Jiang et al., Food Funct. 12:2354-2377 (2021) (Year: 2021).*
Luca et al., Clin. Exp. Immunol., 195:74-85 (2018) (Year: 2018).*
Mirza et al., Multiple Sclerosis Related Dis., 37(101427):1-12 (2020) (Year: 2020).*
Nikitakis et al., Oral Dis., 23:828-837 (2017) (Year: 2017).*

(Continued)

*Primary Examiner* — Thomas J. Visone
(74) *Attorney, Agent, or Firm* — Ballard Spahr LLP

(57) ABSTRACT

Disclosed herein, are methods of detecting multiple sclerosis in a subject by measuring relative abundances of multiple oral microbiota in sample. Also, disclosed herein are methods of treatment and prophylaxis of MS.

8 Claims, 14 Drawing Sheets

(56) References Cited

OTHER PUBLICATIONS

Oezguen et al., Clin. Exp. Rheumatol., 37 (S121):S5-S66 (2019) (Year: 2019).*
Olsen et al., J. Oral Microbiol., 12:1-10 (2019) (Year: 2019).*
Pereira et al., Parkinsonism Related Dis., 38:61-67 (2017) (Year: 2017).*
Schepici et al., Cell Transplant., 28(12):1507-1527 (2019) (Year: 2019).*
Adkins et al., "Docosahexaenoic acid (22:6n-3) Ameliorated the Onset and Severity of Experimental Autoimmune Encephalomyelitis in Mice." Lipids. 54(1): 13-23; 2019.
Atkins, G. et al. "Transient virus infection and multiple sclerosis." Rev Med Virol, 10: 291-303. (2000).
Ballerini et al., "Conditioned medium from relapsing-remitting multiple sclerosis patients reduces the expression and release of inflammatory cytokines induced by LPS-gingivalis in THP-1 and MO3.13 cell lines." Cytokine, 2017; 96: 261-72.
Beecham et al., "Analysis of immune-related loci identifies 48 new susceptibility variants for multiple sclerosis." Nature genetics. 2013; 45(11): 1353-60.
Berer et al., "Gut microbiota from multiple sclerosis patients enables spontaneous autoimmune encephalomyelitis in mice." Proceedings of the National Academy of Sciences of the United States of America. 2017; 114(40): 10719-24.
Bjornevik et al., "Polyunsaturated fatty acids and the risk of multiple sclerosis." Multiple sclerosis, 2017; 23 (14): 1830-8.
Bjornevik et al., "α-Linolenic acid is associated with MRI activity in a prospective cohort of multiple sclerosis patients." Multiple sclerosis, 2019; 25(7): 987-93.
Boaden et al., "Oral flora in acute stroke patients: A prospective exploratory observational study." Gerodontology. 2017; 34(3): 343-56.
Buchfink et al., "Fast and sensitive protein alignment using Diamond." Nature methods, 2015; 12(1): 59-60.
Chen et al., "Microbiota in Human Periodontal Abscess Revealed by 16S rDNA Sequencing." Frontiers in microbiology, 2019; 10: 1723.
Chen et al., "Multiple sclerosis patients have a distinct gut microbiota compared to healthy controls." Scientific reports. 2016; 6: 28484.
Cosorich et al., "High frequency of intestinal TH17 cells correlates with microbiota alterations and disease activity in multiple sclerosis." Science advances, 2017; 3(7): e1700492.
Damgaard et al., "Porphyromonas gingivalis in saliva associates with chronic and aggressive periodontitis." Journal of oral microbiology, 2019; 11(1): 1653123.
Escapa et al., mSystems, 2018; 3:e00187-18.
Furusawa et al., "Commensal microbiota regulates T cell fate decision in the gut." Seminars in immunopathology, 2015; 37(1): 17-25.
Gazdeck et al., "Diversity of the oral microbiome between dentate and edentulous individuals." Oral diseases, 2019; 25(3): 911-8.
George et al., "Multiple sclerosis risk loci and disease severity in 7,125 individuals from 10 studies." Neurology Genetics. 2016; 2(4): e87.
Gil-Varea et al., "Exome sequencing study in patients with multiple sclerosis reveals variants associated with disease course." Journal of neuroinflammation. 2018; 15(1): 265.
Gomez and Nelson, "The Oral Microbiome of Children: Development, Disease, and Implications Beyond Oral Health." Microbial ecology, 2017; 73(2): 492-503.
Huang et al., "Geraniol suppresses proinflammatory mediators in phorbol 12-myristate 13-acetate with A23187-induced HMC-1 cells." Drug design, development and therapy, 2018; 12: 2897-903.
Isobe et al., "Association of HLA Genetic Risk Burden With Disease Phenotypes in Multiple Sclerosis." JAMA neurology. 2016; 73(7): 795-802.
Jiang et al., "Geraniol alleviates LPS-induced acute lung injury in mice via inhibiting inflammation and apoptosis." Oncotarget. 2017; 8(41): 71038-53.

Kanehisa et al., "KEGG: new perspectives on genomes, pathways, diseases and drugs." Nucleic acids research, 2017; 45(D1): D353-D361.
Kim et al. 2016. "Centrifuge: rapid and sensitive classification of metagenomic sequences." Genome Res. 26, 1721-1729.
Kong et al., "New and Preliminary Evidence on Altered Oral and Gut Microbiota in Individuals with Autism Spectrum Disorder (ASD): Implications for ASD Diagnosis and Subtyping Based on Microbial Biomarkers." Nutrients. 2019; 11(9): 2128.
Kuusisto et al., "Concordance and heritability of multiple sclerosis in Finland: study on a nationwide series of twins." European journal of neurology. 2008; 15(10): 1106-10.
Liu et al., "Analysis of Salivary Microbiome in Patients with Alzheimer's Disease." Journal of Alzheimer's disease. 2019; 72(2): 633-40.
Lokmer et al., "Response of the human gut and saliva microbiome to urbanization in Cameroon." Scientific reports, 2020; 10(1): 2856.
Melbye et al., "Short-chain fatty acids and gut microbiota in multiple sclerosis." Acta neurologica Scandinavica, 2019; 139(3): 208-19.
Panza et al., "Time to test antibacterial therapy in Alzheimer's disease." Brain. 2019; 142(10): 2905-29.
Patsopoulos, Genetics of Multiple Sclerosis: An Overview and New Directions. Cold Spring Harbor perspectives in medicine. 2018; 8.
Pereira et al., "Oral and nasal microbiota in Parkinson's disease." Parkinsonism & related disorders, 2017; 38: 61-7.
Polak et al., "Oral infection with P. gingivalis exacerbates autoimmune encephalomyelitis." Journal of periodontology, 2018; 89(12): 1461-6.
Qiao et al., "Alterations of oral microbiota distinguish children with autism spectrum disorders from healthy controls." Scientific reports, 2018; 8(1): 1597.
Ranjan et al., "Analysis of the microbiome: Advantages of whole genome shotgun versus 16S amplicon sequencing." Biochemical and biophysical research communications, 2016; 469(4): 967-77.
Russo et al., "Preliminary Comparison of Oral and Intestinal Human Microbiota in Patients with Colorectal Cancer: A Pilot Study." Frontiers in microbiology, 2017; 8: 2699.
Shapira et al., "Effects of Porphyromonas gingivalis on the central nervous system: activation of glial cells and exacerbation of experimental autoimmune encephalomyelitis." Journal of periodontology. 2002; 73(5): 511-6.
Shaw et al., "The Human Salivary Microbiome Is Shaped by Shared Environment Rather than Genetics: Evidence from a Large Family of Closely Related Individuals." mBio. 2017; 8(5).
Singhrao and Olsen, "Assessing the role of Porphyromonas gingivalis in periodontitis to determine a causative relationship with Alzheimer's disease." Journal of oral microbiology. 2019; 11(1): 1563405.
Smith et al., "The microbial metabolites, short-chain fatty acids, regulate colonic Treg cell homeostasis." Science (New York, NY), 2013; 341(6145), pp. 1-10.
Stewart et al., "Effects of tobacco smoke and electronic cigarette vapor exposure on the oral and gut microbiota in humans: a pilot study." Peer J. 2018; 6: e4693.
Szafranski et al., "High-resolution taxonomic profiling of the subgingival microbiome for biomarker discovery and periodontitis diagnosis." Applied and environmental microbiology, 2015; 81(3): 1047-58.
Tadokoro et al., "Experimental autoimmune encephalomyelitis can be prevented and cured by infection with Trypanosoma cruzi." Journal of autoimmunity, 2004; 23(2): 103-15.
Thompson et al., "Diagnosis of multiple sclerosis: 2017 revisions of the McDonald criteria." The Lancet Neurology, 2018; 17(2): 162-73.
Tremlett et al., "Associations between the gut microbiota and host immune markers in pediatric multiple sclerosis and controls." BMC neurology, 2016; 16(1): 182.
Wallberg and Harris, "Co-infection with Trypanosoma brucei brucei prevents experimental autoimmune encephalomyelitis in DBA/1 mice through induction of suppressor APCs." International immunology. 2005; 17(6): 721-8.

(56) References Cited

OTHER PUBLICATIONS

Zameer et al., "Bisphosphonates: Future perspective for neurological disorders." Pharmacological reports: PR, 2018; 70(5): 900-7.

\* cited by examiner

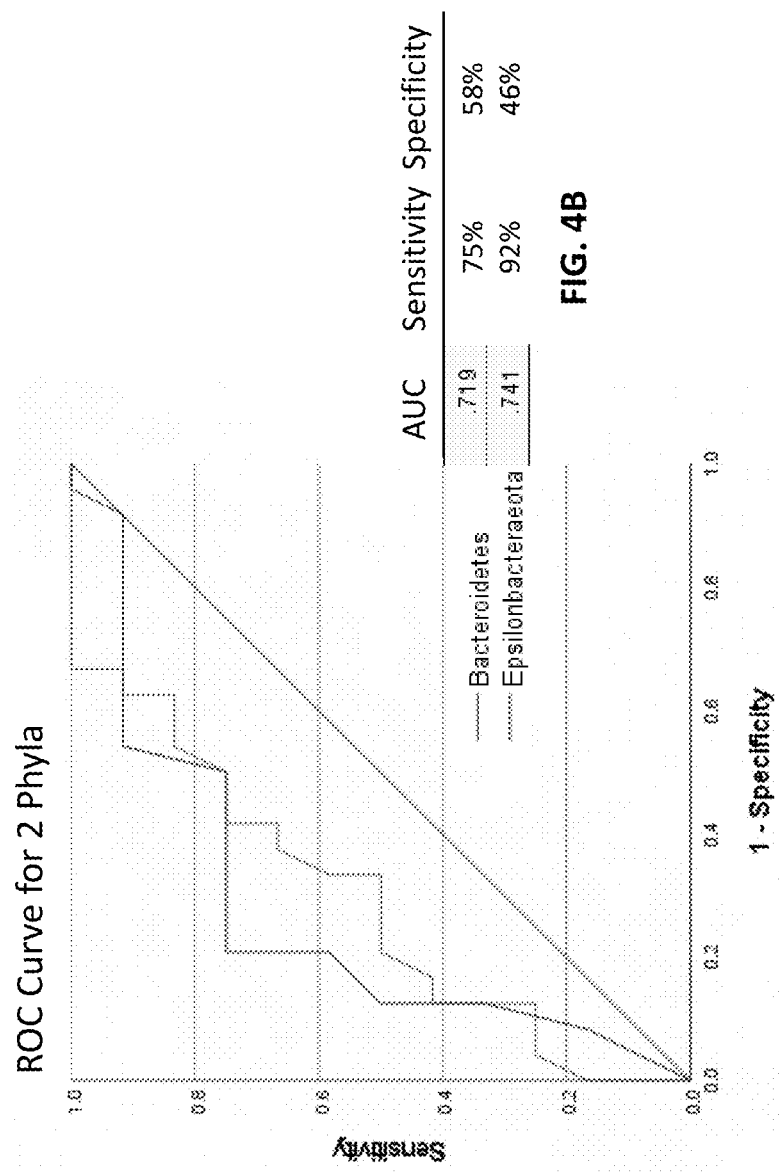

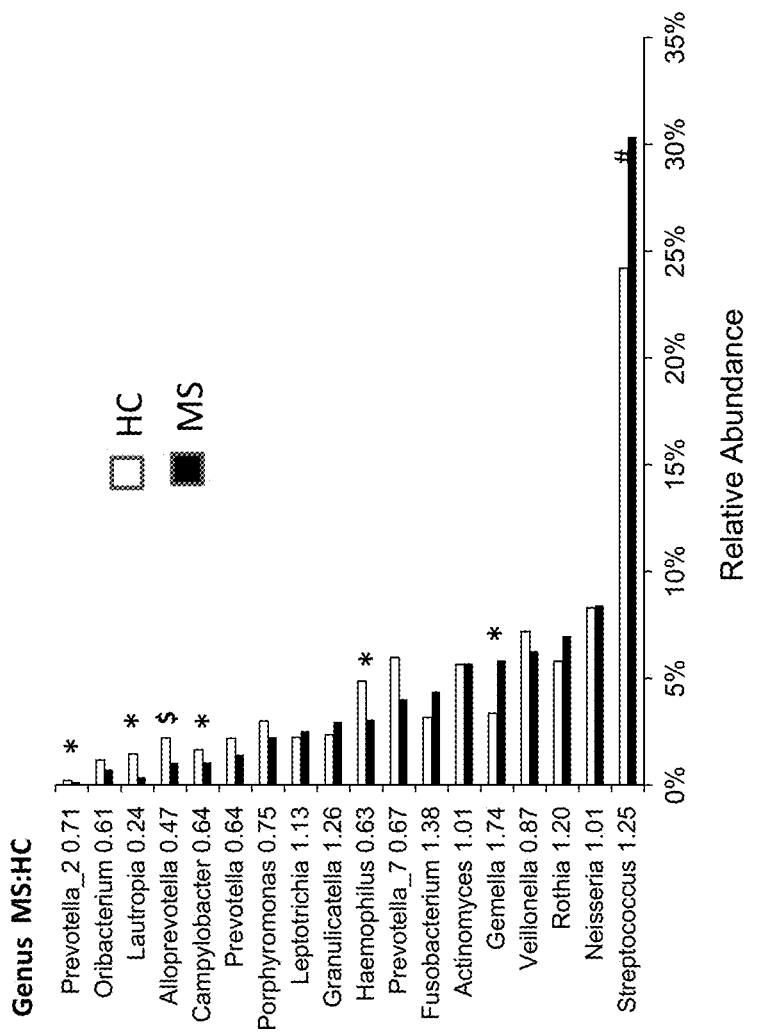

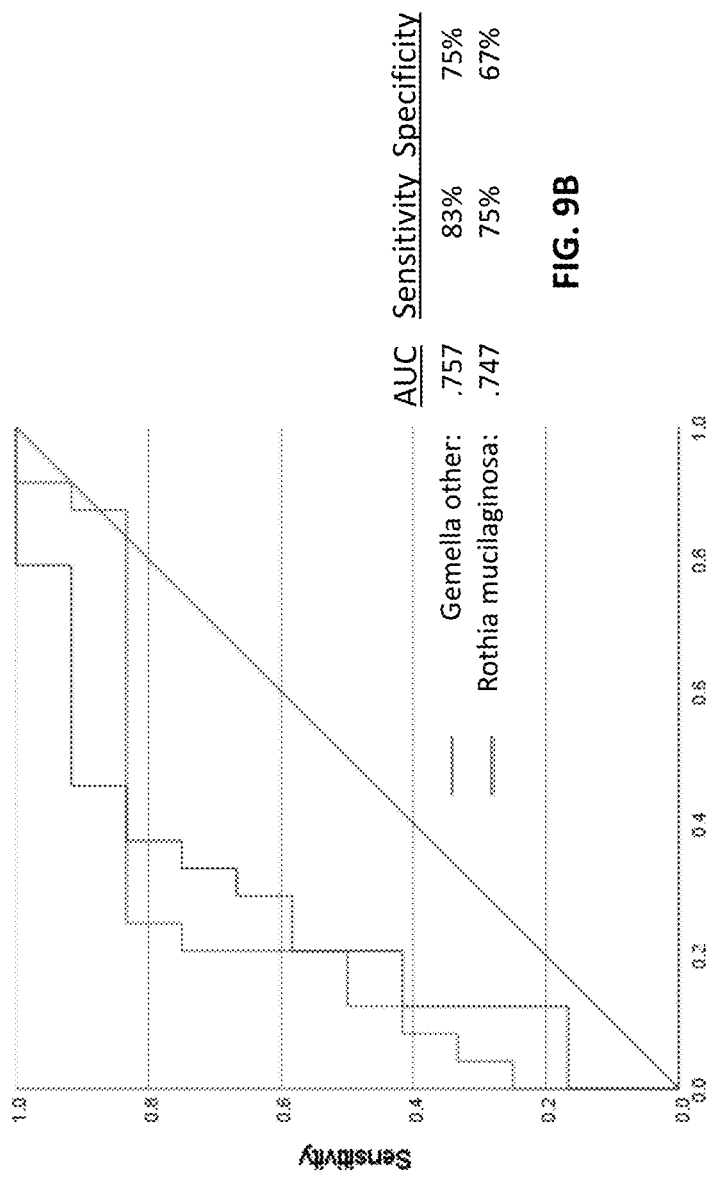

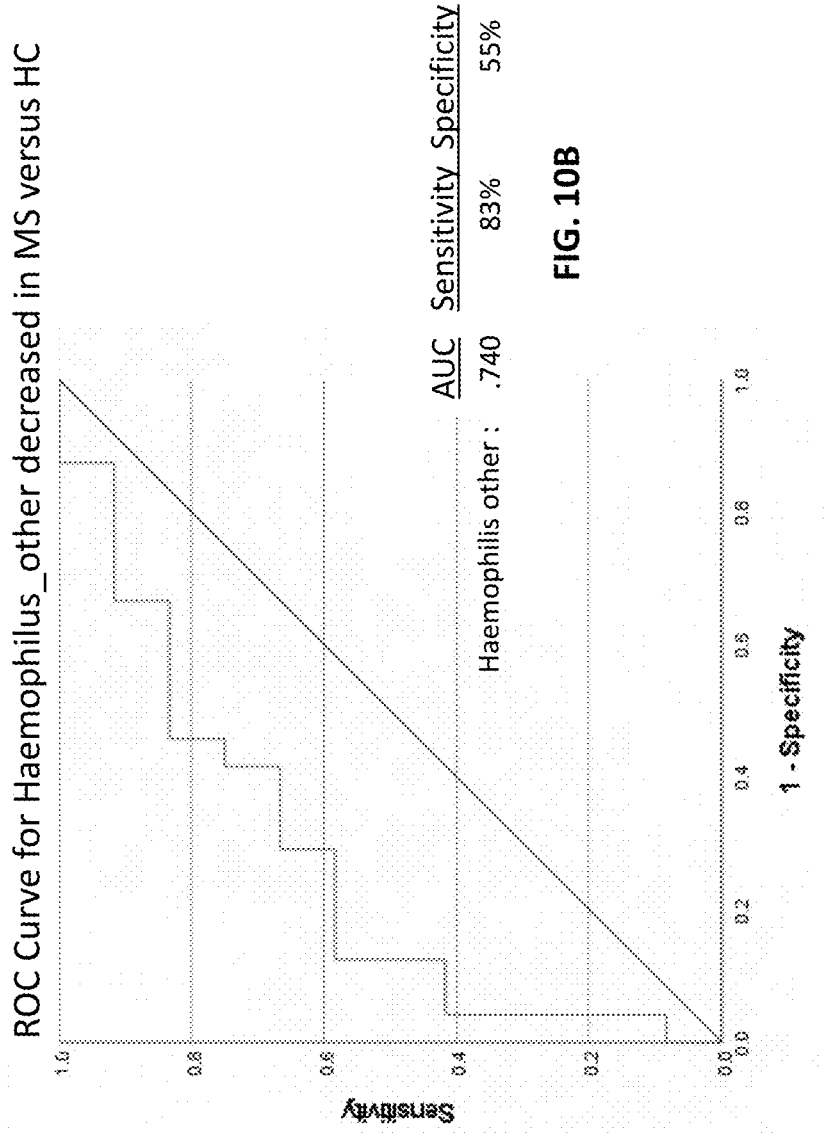

COMPOSITIONS AND METHODS USEFUL IN DETECTING AND DIAGNOSING MULTIPLE SCLEROSIS

CROSS REFERENCE TO RELATED APPLICATIONS

This application claims the benefit of U.S. Provisional Application No. 63/171,789, filed Apr. 7, 2021. The content of this earlier filed application is hereby incorporated by reference herein in its entirety.

STATEMENT REGARDING FEDERALLY FUNDED RESEARCH

This invention was made with government support under grant numbers BX002625 and 14S-RCS-003 awarded by the Department of Veterans Affairs. The government has certain rights in the invention.

BACKGROUND

Multiple Sclerosis (MS) is a chronic demyelinating disease of unknown cause, which affects the brain and spinal cord of about 1,000,000 individuals in the U.S. A number of infections of the central nervous system (CNS) can lead to demyelination, including distemper (dogs), measles (SSPE, humans), JC virus (humans), and influenza (humans) (Atkins, G. et al. *Rev Med Virol*, 291-303. (2000)). The precise etiology of MS remains to be determined.

SUMMARY

Disclosed herein are methods of diagnosing multiple sclerosis (MS) in a subject, the method comprising: obtaining a biological sample from the subject; and detecting in the biological sample an increased abundance of a *Gemella* or *Streptococcus* genus of bacteria or a decreased abundance of a *Haemophilus, Campylobacter, Prevotella_2, Alloprevotella*, or *Lautropia* genus of bacteria relative to that of a biological sample obtained from a control subject, thereby diagnosing MS in the subject.

Disclosed herein are methods of diagnosing and treating multiple sclerosis (MS) in a subject, the methods comprising: a) obtaining a biological sample from the subject; b) detecting in the biological sample an increased abundance of a *Gemella* or *Streptococcus* genus or species of bacteria or a decreased abundance of a *Haemophilus, Campylobacter, Prevotella_2, Alloprevotella*, or *Lautropia* genus or species of bacteria relative to that of a biological sample obtained from a control subject, thereby diagnosing MS in the subject; and c) administering to the subject diagnosed with MS a salivary microbiome altering agent to support growth of *Haemophilus, Campylobacter, Prevotella_2, Alloprevotella*, or *Lautropia* genus or species, to reduce growth of *Gemella* or *Streptococcus* genus or species, an MS therapeutic, or a combination thereof.

Disclosed herein are methods of treating a patient with multiple sclerosis (MS), the methods comprising: administering to the patient with MS a salivary microbiome altering agent to reduce growth of *Gemella* or *Streptococcus* genus or species, to support growth of *Haemophilus, Campylobacter, Prevotella_2, Alloprevotella*, or *Lautropia* genus or species, an MS therapeutic agent, or a combination thereof to the subject, wherein the patient is identified as needing the MS a salivary microbiome altering agent, the MS therapeutic agent, or a combination thereof by a) obtaining a biological sample from the patient; and b) detecting in the biological sample an increased amount of a *Gemella* or *Streptococcus* genus or species of bacteria or a decreased amount of a *Haemophilus, Campylobacter, Prevotella_2, Alloprevotella*, or *Lautropia* genus or species of bacteria relative to that of a biological sample obtained from a control subject.

Disclosed herein are methods of measuring the probability of a subject developing or having multiple sclerosis (MS), the methods comprising: a) obtaining a biological sample from the subject; b) measuring the abundance of at least *Gemella* or *Streptococcus* genus or species of bacteria and *Haemophilus, Campylobacter, Prevotella_2, Alloprevotella*, or *Lautropia* genus or species of bacteria; and c) determining the probability of a subject developing or having multiple sclerosis (MS) based on the abundance of at least *Gemella* or *Streptococcus* genus or species of bacteria and *Haemophilus, Campylobacter, Prevotella_2, Alloprevotella*, or *Lautropia* genus or species of bacteria, wherein an increased abundance of a *Gemella* or *Alloprevotella* species of bacteria or a decreased amount of a *Haemophilus, Campylobacter, Prevotella_2, Alloprevotella*, or *Lautropia* genus or species of bacteria relative to that of a biological sample obtained from a control subject, indicates a high probability of the subject developing or having MS.

BRIEF DESCRIPTION OF THE DRAWINGS

The accompanying figures, which are incorporated in and constitute a part of this specification, illustrate several aspects and together with the description serve to explain the principles of the invention.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

(FIG. 2A) Level 1; (FIG. 2B) Level 2; (FIG. 2C) Level 3 hierarchies. The KEGG identifiers are provided for the hierarchies.

FIGS. 4A-B shows the receiver operator characteristic (ROC) curve showing sensitivity and 1-specificity for detection of MS patients versus HCs for 2 phylum that are significantly decreased in the MS group (FIG. 4A) AUC, area under the curve; and FIG. 4B shows maximum values for sensitivity and specificity derived from ROC curve coordinates.

FIG. 5 shows the relative abundance of bacterial Genera in MS patients and healthy controls (HC) for genera present at 1% or higher, and for *Prevotella_2* which is significantly different between groups. *, P<0.05; $, P<0.06 Mann Whitney U test; #, P<0.06, parametric T-test, excluding 2 PPMS patients.

FIG. 6B shows the maximum values for sensitivity and specificity derived from ROC curve coordinates.

FIG. 7B shows the maximum values for sensitivity and specificity derived from ROC curve coordinates.

FIGS. 9A-B show receiver operator characteristic (ROC) curve showing sensitivity and 1-specificity for detection of MS patients versus HCs for 2 species which are increased in MS versus HC (FIG. 9A). AUC, area under the curve; FIG. 9B shows maximum values for sensitivity and specificity derived from ROC curve coordinates.

FIGS. 10A-B show receiver operator characteristic (ROC) curve showing sensitivity and 1-specificity for detection of MS patients versus HCs for *Haemophilus_other* which is decreased in MS versus HC (FIG. 10A). AUC, area under the curve; FIG. 10B shows maximum values for sensitivity and specificity derived from ROC curve coordinates.

FIG. 11A shows the ratio of average relative abundance (RA) in MS to HC groups, for the 7 genera found significantly different between the MS versus HC groups. FIG. 11B shows for each MS patient (n=12) the number of times the ratio of the RA for each of the 7 genera compared to the average RA for the HC group showed the same change (increased or decreased) as the entire MS group. Note that for the 2 PPMS subjects (S1, S2) 5 of the 7 genera were found significantly different (*, *Prevotella* and *Staphylococcus* were only different comparing RRMS to HC.

DETAILED DESCRIPTION

Figures 1A, 1B:
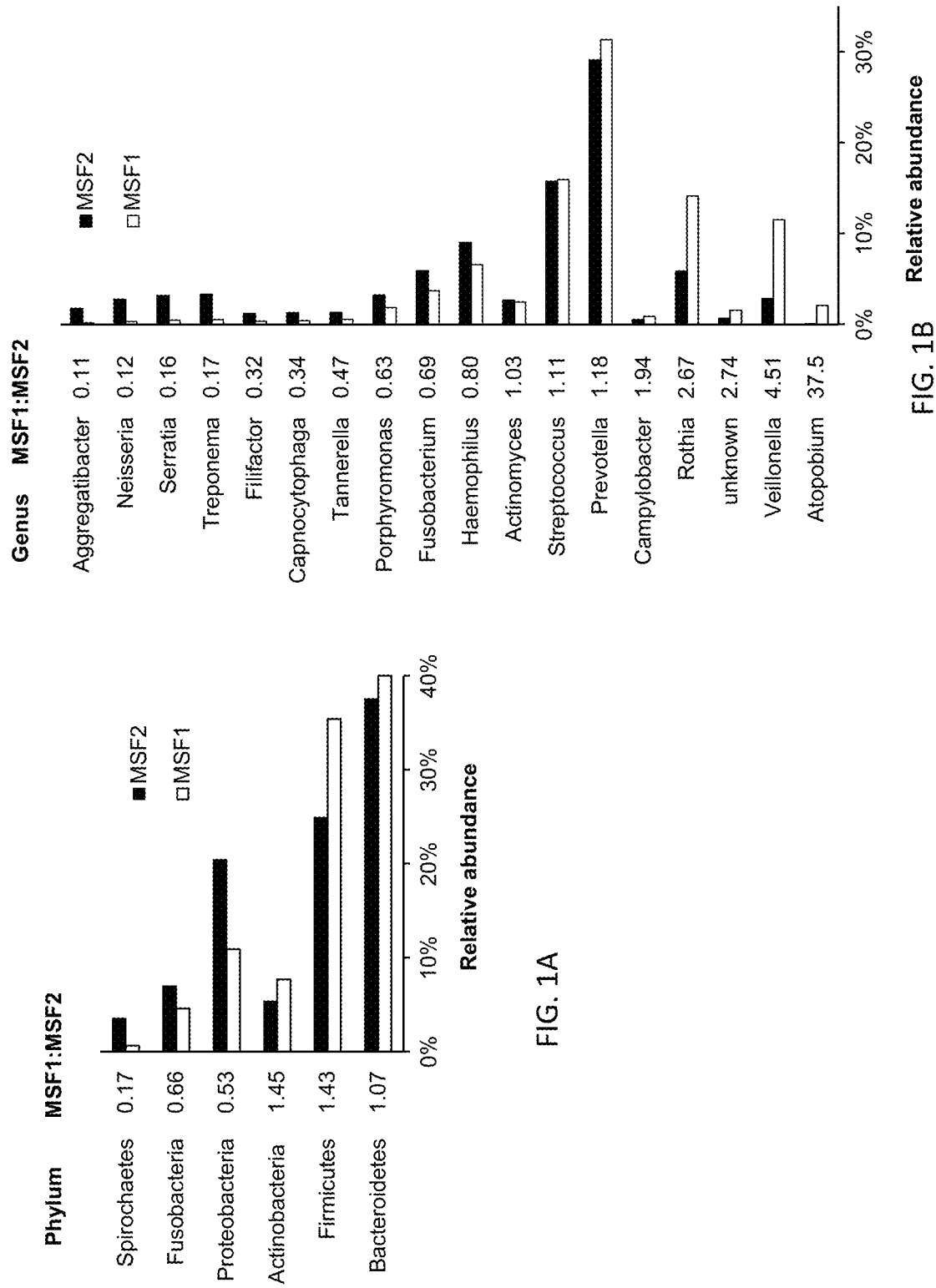
FIG. 1A-C show relative taxa abundance in monozygotic twins discordant for MS severity. Total reads were summed for each unique (FIG. 1A) phylum, (FIG. 1B) genus, and (FIG. 1C) species present in saliva DNA isolated from MSF1 and MSF2. For genus and species present at 1% or greater abundance are shown. The ratio of reads in MSF1 compared to MSF2 is shown.

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile, cerebral spinal fluid) that contains cells or cell components. In some aspects, the sample can be taken from the brain, spinal cord, cerebral spinal fluid or blood.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In some aspects, a subject can be a mammal. In some aspects, a subject can be a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for multiple sclerosis, such as, for example, prior to the administering step.

As used herein, the term "normal" refers to an individual, a sample or a subject that does not have multiple sclerosis or does not have an increased susceptibility of developing multiple sclerosis.

As used herein, the term "susceptibility" refers to the likelihood of a subject developing or being clinically diagnosed with a disease. For example, a human subject with an increased susceptibility for multiple sclerosis can refer to a human subject with an increased likelihood of a subject developing or being clinically diagnosed with multiple sclerosis.

As used herein, the term "comprising" can include the aspects "consisting of" and "consisting essentially of."

By "specifically binds" is meant that an antibody recognizes and physically interacts with its cognate antigen (for example, a microbe-specific antibody is an antibody are specific to one or more microbes disclosed herein) and does not significantly recognize and interact with other antigens; such an antibody may be a polyclonal antibody or a monoclonal antibody, which are generated by techniques that are well known in the art.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for a microbe-specific antibody and have at least 80%-90% sequence complementarity, preferably at least 91%-95% sequence complementarity, more preferably at least 96%-99% sequence complementarity, and most preferably 100% sequence complementarity to the region of the microbe-specific antibody to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (that is, base-pairs) with a substantially complementary nucleic acid (for example, a microbe-specific antibody) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, NY, 1998). The term "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, a "control" is a sample from either a normal subject (e.g., a subject without multiple sclerosis) or from tissue that is not demyelinating or demyelinated.

As used herein, "over-expression" means expression greater than the expression detected in normal tissue. For example, a nucleic acid that is over-expressed may be expressed about 1 standard deviation above normal, or about 2 standard deviations above normal, or about 3 standard deviations above the normal level of expression. Therefore, a nucleic acid that is expressed about 3 standard deviations above a control level of expression is a nucleic acid that is over-expressed.

As used herein, the term "treat" or "treatment" refers to the medical management of a patient with the intent to cure, ameliorate, stabilize, or prevent a disease, pathological condition, or disorder (e.g., multiple sclerosis). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease (e.g., multiple sclerosis).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, "prevent" is meant to mean minimize the chance that a subject who has an increased susceptibility for developing multiple sclerosis will develop multiple sclerosis.

As used herein, the term "reference," "reference expression," "reference sample," "reference value," "control," "control sample" and the like, when used in the context of a sample or expression level of one or more microbes refers to a reference standard wherein the reference is expressed at a constant level among different samples, and is unaffected by the experimental conditions, and is indicative of the level in a sample of a predetermined disease status (e.g., not suffering from a multiple sclerosis). The reference value can be a predetermined standard value or a range of predetermined standard values, representing no illness, or a predetermined type or severity of illness.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with multiple sclerosis" means having been subjected to an examination by a person of skill, for example, a physician, and found to have multiple sclerosis that can be diagnosed or treated by a compound or composition disclosed herein.

As used herein, the term "microbe" refers to a microscopic organism (i.e., a living thing that is too small to be seen with the naked eye). Generally, the term "microbe" is used to describe different life forms that can have different sizes and characteristics. For example, a microbe can refer to bacteria, archaea, fungi, protists, viruses and microscopic animals.

The word "other" as used herein in connection with a bacterial species in a specific genus refers to the identification of a unique DNA sequence for a species that has not yet been formally classified; or to a DNA sequence which contains ambiguity preventing distinction between 2 or more unique species'

Microbiomes and Detection Thereof

Identifying changes that occur in the microbiome (biome, microflora) which influence the onset, severity, or resolution of disease is of current interest. The majority of biome studies use DNA samples present in gut, and the easiest way to obtain those is from fecal samples. Alternatively, studies are using DNA samples isolated from the oral cavity, such as buccal tissue or saliva. This provides easier accessibility to samples, as well as being more palatable to patients. As disclosed herein, the analysis of the microbiome in saliva samples from multiple sclerosis (MS) patients is distinct from that of matched healthy controls (HCs). The ability to rapidly and easily identify biomarkers in the saliva of MS patients will help address the related problems of needing better diagnostics to detect disease onset; ways to monitor disease progression; ways to monitor the efficacy of therapeutic interventions; providing a prognostic tool to estimate disease duration or severity; and helping to identify novel targets for therapeutic intervention.

Genetic analysis of the bacteria species in different human tissues has been carried out for over 50 years; currently it is done either using a next generation sequencing (NGS) approach or a targeted amplification of bacterial 16S ribosomal RNA. The above methods have been used to explore changes in the microbiome in a number of diseases and conditions, including neurological diseases such as AD, PD, as well as MS; and differences between patients and controls have been reported. However, in the majority of these studies, the gut microbiome was analyzed using DNA isolated from fecal samples. Described herein is a comparison using the oral (salivary) biome of MS patients to matched healthy controls. The results demonstrate differences between MS patients and controls evidencing that some of the differences may be associated with disease severity.

Disclosed herein are also methods that can be used alone or in combination with the methods described herein that can be used to identify an abundance of one or more genus of microbes in a sample and determining the disease or disease state based on the measured abundances.

Disclosed herein are also methods that can be used alone or in combination with the methods described herein that can be used to identify an abundance of one or more species of microbes in a sample and determining the disease or disease state based on the measured abundances.

Described herein is the observed association of microbiota, and in particular, saliva microbiota and multiple sclerosis. The results show that MS patients have an altered microbiome when compared to matched control subjects.

Described herein are methods of detecting several related demyelinating disorders including, but not limited to neuromyelitis optics (NMO),
acute disseminated encephalomyelitis (ADEM), clinically isolated syndrome (CIS), radiologically isolated syndrome (CIS) and MS, including primary progressive MS (PPSM), relapsing remitting MS (RRMS), and secondary progressive MS (SPMS).

Disclosed herein are methods relating to diagnostics of MS. The methods are rapid, non-invasive and easy to use. The present invention provides a considerable advantage of enabling the individuals having or being at risk of developing MS being diagnosed at an early stage preferably before impaired coordination appears or before MS patients experience a flare-up or relapse. Once diagnosed at an early stage or before a flare-up as belonging to the risk group, the onset of MS or MS flare up in the individual can be prevented by modifying the community structure of the saliva or gut microbiota. The present invention specifically provides methods for preventing MS or a MS flare-up in a subject and also means for slowing the disease process or even stopping it. The combination of the methods and the compositions permit the development of personalized treatment and possibly personalized dietary guidance.

Disclosed herein are methods, wherein the probability of a subject developing or having MS or a MS flare-up or relapse is determined by a method wherein a sample is obtained from a subject; relative abundances of one or more microbial taxa in the sample are measured; and probability of the subject developing or having MS or a MS flare-up is determined based on the measured relative abundances of one or multiple microbial taxa in the sample.

The present invention concerns generally demyelinating disorders, multiple sclerosis and also multiple sclerosis that involves an immune-mediated response of the body's immune system that is directed against the central nervous system causing variable and unpredictable symptoms. MS causes many different symptoms, including vision loss, pain, fatigue, and impaired coordination. It is currently not possible to predict how multiple sclerosis will progress in any individual. Some people have mild symptoms, such as blurred vision and numbness and tingling in the limbs. In severe cases, a person may experience paralysis, vision loss, and mobility problems.

Methods

Disclosed herein are methods of diagnosing and/or detecting multiple sclerosis (MS) in a subject. The methods disclosed herein can be useful for making a microbiological diagnosis. In some aspects, the methods disclosed herein can be used to distinguish early stage multiple sclerosis from clinically isolated syndrome or radiological isolated syndrome. In some aspects, the methods disclosed herein can be used to distinguish relapsing-remitting multiple sclerosis from secondary-progressive multiple sclerosis. In some aspects, the methods disclosed herein can be used to distinguish relapsing-remitting multiple sclerosis and secondary-progressive multiple sclerosis from primary progressive types of multiple sclerosis.

In some aspects, the methods can comprise obtaining a biological sample from the subject. In some aspects, the methods can comprise detecting in a biological sample an increased abundance of a *Gemella* or *Streptococcus* genus of bacteria or a decreased abundance of a *Haemophilus, Campylobacter, Prevotella_2, Alloprevotella*, or *Lautropia* genus of bacteria relative to that of a biological sample obtained from a control subject, thereby diagnosing and/or detecting MS in the subject. In some aspects, two or more changes in abundance of *Gemella* or *Streptococcus* genus of bacteria and/or *Haemophilus, Campylobacter, Prevotella_2, Alloprevotella*, or *Lautropia* genus of bacteria are detected relative to that of a biological sample obtained from a control subject, thereby diagnosing and/or detecting MS in the subject. In some aspects, the detecting step can comprise detecting in the biological sample a decreased abundance of a *Haemophilus, Campylobacter*, and *Prevotella_2* genus or species of bacteria relative to that of a biological sample obtained from a control subject, thereby diagnosing MS in the subject.

In some aspects, the methods can comprise detecting in a biological sample an increased abundance of a *Gemella, Staphylococcus* or *Streptococcus* species of bacteria or a decreased abundance of a *Haemophilus, Campylobacter, Prevotella_2, Alloprevotella*, F0058, or *Lautropia* species of bacteria relative to that of a biological sample obtained from a control subject, thereby diagnosing and/or detecting MS in the subject. In some aspects, two or more changes in abundance of *Gemella, Staphylococcus* or *Streptococcus* species of bacteria and/or *Haemophilus, Campylobacter, Prevotella_2, Alloprevotella*, F0058, or *Lautropia* species of bacteria are detected relative to that of a biological sample obtained from a control subject, thereby diagnosing and/or detecting MS in the subject.

In some aspects, the *Gemella* species of bacteria can be *Gemella* other. In some aspects, the *Haemophilus* species of bacteria can be *Haemophilus* other. In some aspects, the *Campylobacter* species of bacteria can be *Campylobacter* other. In some aspects, the methods can comprise detecting in a biological sample an increased abundance of *Gemella* Other, *Neisseria* Other, *Rothia mucilaginosa, Solobacterium moorei* or a combination thereof relative to that of a biological sample obtained from a control subject, thereby diagnosing and/or detecting MS in the subject. In some aspects, the methods can comprise detecting in a biological sample an decreased abundance of *Campylobacter* Other, *Bergeyella* Other, *Treponema_2 socranskii, Selenomonas sputigena* or a combination thereof relative to that of a biological sample obtained from a control subject, thereby diagnosing and/or detecting MS in the subject.

In some aspects, detecting of the increased abundance of the *Gemella* or *Streptococcus* genus of bacteria or the decreased abundance of a *Haemophilus, Campylobacter, Prevotella_2, Alloprevotella*, or *Lautropia* genus of bacteria includes at least one assay selected from the group consisting of nucleic acid sequencing, PCR amplification, a competitive binding assay, a non-competitive binding assay, a radioimmunoassay, immunohistochemistry, an enzyme-linked immunosorbent assay (ELISA), a sandwich assay, a gel diffusion immunodiffusion assay, an agglutination assay, dot blotting, a fluorescent immunoassay such as fluorescence-activated cell sorting (FACS), a chemiluminescence immunoassay, an immunoPCR immunoassay, a protein A or protein G immunoassay, and an immunoelectrophoresis assay. In some aspects, the methods can further comprise obtaining a sample of T cells from the subject to identify T cells specific for the *Gemella, Streptococcus, Haemophilus, Campylobacter, Prevotella_2, Alloprevotella*, or *Lautropia* genus of bacteria in the subject. In some aspects, the methods can include obtaining a second biological sample, wherein the second biological sample is saliva, blood, serum, or plasma. In some aspects, the methods can further comprise detecting and identifying one or more specific bacterially-derived products and their metabolic derivatives, from *Gemella, Streptococcus, Haemophilus, Campylobacter, Prevotella_2, Alloprevotella*, or *Lautropia* genus or species of in the subject. Examples of bacterial products can include but are not limited to phytoestrogen metabolites including isoflavones, coumestans, prenylflavonoids, flavonols, and lignans; Short Chain Fatty Acids (SCFAs) including butyrate, butyric acid, iso-butyric acid, propionic acid, acetic acid, valeric acid, isovaleric acid, isocaproic acid, trimethylamine N-oxide, 3-hydroxybenzoic acid, 3,4-dihydroxybenzoic acid, dihydrocaffeic acid, indoxyl sulfate, 4-ethylphenylsulfate; and amino acid metabolites including tyrosine and tryptophan metabolites (tryptamine, kynurenine, quinolate, indoles).

In some aspects, the probability of the subject developing or having MS or an MS flare-up can be determined based on the measured relative abundances of one or multiple microbial taxa in the sample. The high relative abundance can be defined as being higher as a reference value, which is a predefined threshold value, and vice versa. Relative abundance means the abundance of a microbial taxon relative to the sum of the abundances of all taxa detected in a sample.

A reference sample can be a sample from an individual not having MS or having a low risk of developing MS. Indicators of low risk are e.g., no strong family history of MS. In some aspects, taxa abundances in reference samples including samples from MS patients can be used to generate a logistic regression model, wherein the probability of developing or having MS is modelled as a function of taxa abundances. The value of a logistic regression classifier is calculated based on said logistic regression model and the values of the subject. The value of said logistic regression classifier is then used to determine the probability of the subject developing or having MS.

The relative abundance of a microbial taxa can be measured using techniques based on DNA sequencing, quantitative PCR, DNA microarray, by using test beds utilizing arrays or other suitable platforms including microfluidistic solutions, techniques based on droplet PCR, quantitative PCR, or any other suitable method wherein the abundance of taxa can be expressed as read count, percentage, cell count, or value expressing intensity of any other suitable signal. In some aspects, the amount or relative abundance of any of the taxa disclosed herein can be determined by nucleic acid sequencing. In some aspects, the relative abundance of *Gemella, Streptococcus, Haemophilus, Campylobacter, Prevotella_2, Alloprevotella*, or *Lautropia* genus or related species of bacteria can be determined by nucleic acid sequencing. In some aspects, the nucleic acid sequencing can be determined using 16S rRNA amplicon sequencing. In some aspects, the nucleic acid sequencing can be determined using quantitative PCR.

A microbial taxon as used herein refers to a taxonomic unit, whether named or not: i.e., a population, or group of populations of organisms which are usually inferred to be
  phylogenetically related and which have characters in
    common which differentiate the unit (e.g., a genus, a family) from other such units. A taxon encompasses the included taxa of
  lower rank and individual organisms. The term as used herein furthermore includes termed species-level phylotypes or operational taxonomic units that are identified by their complete 16S rRNA sequence and usually defined as sharing 97% or less sequence identity with other entries in the ribosomal databases. In some aspects, the measurement of relative abundances of microbial taxa can include all taxa that can be identified in a sample.

In some aspects, the relative abundances can be determined for one or microbial taxa including but not limited to *Gemella, Streptococcus, Haemophilus, Campylobacter, Prevotella_2, Alloprevotella*, or *Lautropia*. In some aspects, an increased (or high) relative abundance of *Gemella, Staphylococcus*, or *Streptococcus* can indicate a high probability of the subject developing or having multiple sclerosis. In some aspects, an increased (or high) relative abundance of *Gemella* Other, *Neisseria* Other, *Rothia mucilaginosa*, or *Solobacterium moorei* can indicate a high probability of the subject developing or having multiple sclerosis. In some aspects, a decreased (or low) relative abundance of *Haemophilus, Campylobacter, Prevotella_2, Alloprevotella, Lautropi*, or F0058 can indicate a high probability of the subject developing or having multiple sclerosis. In some aspects, a decreased (or low) relative abundance of *Campylobacter* Other, *Bergeyella* Other, *Haemophilus* Other, *Treponema_2 socranskii*, or *Selenomonas sputigena* can indicate a high probability of the subject developing or having multiple sclerosis. In some aspects, an increased (or high) relative abundance of *Gemella, Staphylococcus*, or *Streptococcus* or *Gemella* Other, *Neisseria* Other, *Rothia mucilaginosa*, or *Solobacterium moorei* and a decreased (or low) relative abundance of *Haemophilus, Campylobacter, Prevotella_2, Alloprevotella, Lautropi*, or F0058 or *Campylobacter* Other, *Bergeyella* Other, *Haemophilus* Other, *Treponema_2 socranskii*, or *Selenomonas sputigena* can indicate a high probability of the subject developing or having multiple sclerosis.

In some aspects, the methods can further include clinically measuring patient symptoms that may include, but are not limited to quantitative measurements of clinical severity using the Enhanced Disability Disease Score (EDSS) or the MS Functional Composite (MSFC) score, or the MS Severity Scale (MSSS) score to quantify changes in MS severity over time; of radiological features using magnetic resonance imaging (MRI) to quantify lesion burden and brain volume, or diffusion weighted imaging (DWI) to quantify white matter tract integrity and axonal damage, or MRI combined with gadolinium administration to quantify integrity of the blood brain barrier; of oligoclonal bands in CSF to quantify the number and isotype of bands; of the immunoglobulin G (IgG) index to quantify the ratio of CSF to blood concentration of IgG; of serum protein levels for established MS biomarkers including for neurofilament light chain (NFL) and for concentrations of pro-inflammatory cytokines including tumor necrosis factor-alpha (TNFa), Interleukin 1b (IL1b) and interferon-gamma (IFNg); and for levels or activity of damaging lymphocytes including Th1 and Th17 type cells and of beneficial lymphocytes including regulatory T cells.

In some aspects, the methods can comprise measuring taxa abundances from reference samples including samples from MS patients and healthy controls and abundances from the sample of the subject can be subjected to a statistical classification method such as, but not limited to "partitioning around the medoid" and "Dirichlet multinomial mixture", that assigns samples into groups based on their taxonomic composition (Arumugam et al., 2011). If the method from a statistical classification assigns the subject's sample to a group containing few MS samples, the probability of the subject developing or having MS can be determined to be low and vice versa. Also, if the method from a statistical classification assigns the subject's sample to a group where the samples have higher abundances of one or more of a specifically disclosed taxa as compared to the other taxa groups the probability of the subject developing or having MS can be determined to be low.

In some aspects, the methods described herein can be used for determining a clinical subtype or disease stage of a MS patient. The methods can comprise obtaining a sample from a subject; determining the abundance of one or multiple of the following taxa: *Gemella, Streptococcus, Haemophilus, Campylobacter, Prevotella_2, Alloprevotella, Staphylococcus*, or *Lautropia* in the sample; and by using statistical methods determining a MS subtype or stage based on the measured abundances. The determination of disease subtypes can be a useful tool to improve research methods and thus can be used to find a cure or better treatments, or help to counsel patients or direct existing therapies. In some aspects, comparison the relative abundances of the oral microbiome can be used, for example to distinguish RRMS from CIS. In some aspects, a *Campylobacter, Rothia, Veillonella*, and *Atopobium* can have a 2-fold or more greater relative abundance in a subject with RRMS; and *Aggregatibacter, Neisseria, Serratia, Treponema, Filifactor*, and *Capnocytophaga* can have a 2-fold or more greater relative abundance in the CIS. In some aspects, changes in relative abundance or species can also be used to distinguish RRMS from CIS. In some aspects, a relative abundance of at least 1% can be detected, for example, in *Prevotella melaninogenica, Rothia mucilaginosa, Streptococcus parasanguinis, Veillonella parvula, Veillonella atypica, Prevotella scopos, Atopobium parvulum*, and *Actinomyces meyeri* at least 2-fold greater relative abundance in the RRMS; and *Prevotella intermedia, Haemophilus parainfluenzae, Streptococcus mitis, Prevotella fusca, Porphyromonas gingivalis, Serratia marcescens, Fusobacterium periodonticum, Fusobacterium nucleatum, Streptococcus oralis, Treponema denticola, Prevotella denticola, Haemophilus influenzae, Streptococcus pneumoniae, Aggregatibacter aphrophilus, Neisseria sicca, Tannerella forsythia, Filifactor alocis*, and *Streptococcus anginosus* can be present at least 2-fold greater relative abundance in CIS.

Disclosed herein are methods of diagnosing and/or detecting a multiple sclerosis in a subject. The methods disclosed herein can be useful for making a microbiological diagnosis. The detection methods described herein can be performed directly via PCR amplification of a nucleic acid or via direct detection using antibodies or peptides that specifically bind one or more of the disclosed microbes. The detection methods described herein can also be performed by detecting antibodies or T-cells specific to one or more of the microbe-specific antibodies.

Also disclosed herein are methods of diagnosing and treating multiple sclerosis (MS) in a subject. In some aspects, the methods can comprise: a) obtaining a biological sample from the subject; b) detecting in the biological sample an increased abundance of a *Gemella* or *Streptococcus* genus or species of bacteria or a decreased abundance of a *Haemophilus*, *Campylobacter*, *Prevotella_2*, *Alloprevotella*, or *Lautropia* genus or species of bacteria relative to that of a biological sample obtained from a control subject, thereby diagnosing MS in the subject; c) administering to the subject diagnosed with MS a salivary microbiome altering agent to support growth of *Haemophilus*, *Campylobacter*, *Prevotella_2*, *Alloprevotella*, or *Lautropia* genus or species, to reduce growth of *Gemella* or *Streptococcus* genus or species, an MS therapeutic, or a combination thereof.

Further disclosed herein are methods of measuring the probability of a subject developing or having multiple sclerosis (MS). In some aspects, the methods can comprise: a) obtaining a biological sample from the subject; b) measuring the abundance of at least *Gemella* or *Streptococcus* genus or species of bacteria and *Haemophilus*, *Campylobacter*, *Prevotella* 2, *Alloprevotella*, or *Lautropia* genus or species of bacteria; and c) determining the probability of a subject developing or having multiple sclerosis (MS) based on the abundance of at least *Gemella* or *Streptococcus* genus or species of bacteria and *Haemophilus*, *Campylobacter*, *Prevotella_2*, *Alloprevotella*, or *Lautropia* genus or species of bacteria. In some aspects, an increased abundance of a *Gemella* or *Streptococcus* species of bacteria or a decreased amount of a *Haemophilus*, *Campylobacter*, *Prevotella_2*, *Alloprevotella*, or *Lautropia* genus species of bacteria relative to that of a biological sample obtained from a control subject, can indicate a high probability of the subject developing or having MS.

Also disclosed herein are methods of treating a subject at risk for developing multiple sclerosis, treating a subject with multiple sclerosis or treating a subject suspected of having multiple sclerosis. Once the relative abundances of *Gemella*, *Streptococcus*, *Haemophilus*, *Campylobacter*, *Prevotella_2*, *Alloprevotella*, or *Lautropia* genus or species are determined, an appropriate treatment can be provided or administered.

In some aspects, the methods can comprise administering to the subject diagnosed with MS a salivary microbiome altering agent to support growth of *Haemophilus*, *Campylobacter*, *Prevotella_2*, *Alloprevotella*, or *Lautropia*. In some aspects, the subject can be identified as needing a salivary microbiome altering agent. In some aspects, the subject can be identified by: obtaining a biological sample from the subject, and detecting in the biological sample an increased abundance of a *Gemella* or *Streptococcus* genus or species of bacteria or a decreased abundance of a *Haemophilus*, *Campylobacter*, *Prevotella_2*, *Alloprevotella*, or *Lautropia* genus or species of bacteria relative to that of a biological sample obtained from a control subject.

In some aspects, the methods can further comprise administering a disease-modifying therapy. In some aspects, the disease-modifying therapy can be a multiple sclerosis therapeutic. Examples of disease-modifying therapies or multiple sclerosis therapeutics include but are not limited to Avonex® (interferon beta-1a), Betaseron® (interferon beta-1b), Copaxone® (glatiramer acetate), Glatopa® (generic Copaxone), Extavia® (interferon beta-1b), Kesimpta® (ofatumumab), Plegridy® (peginterferon beta-1a), Rebif® (interferon beta-1a); Aubagio® (teriflunomide), Bafierta™ (monomethyl fumarate), Tecfidera® (dimethyl fumarate), Dimethyl Fumarate (generic Tecfidera), Gilenya® (fingolimod), Mavenclad® (cladribine), Mayzent® (siponimod), Vumerity® (diroximel fumarate), or Zeposia® (ozanimod); Lemtrada (alemtuzumab), Novantrone (mitoxantrone), Ocrevus® (ocrelizumab), or Tysabri® (natalizumab).

In some aspects, the methods can include measuring the relative abundances of one or more microbial taxa in a biological sample. A biological sample can be a microbial sample taken or obtained from an individual. In some aspects, the biological sample can be a saliva sample. In some aspects, the biological sample can be a muccal swab or other oral-derived sample. In some aspects, the biological sample can be a feces sample. Samples can range from less than a milliliter and can further range in bacterial concentration.

Salivary microbiome is nonpathogenic, commensal bacterial present in the salivary glands. It is distinct from bacteria that may cause infection in the glands. The salivary microbiota, comprising bacteria shed from oral surfaces, has been shown to be individualized, temporally stable and influenced by diet and lifestyle. Salivary microbiota reflects local bacterial alterations of the supragingival and subgingival microbiota.

In any of the methods disclosed herein, the subject can be suspected of having a multiple sclerosis or a multiple sclerosis flare-up. In any of the methods disclosed herein, the subject can be at risk of having multiple sclerosis or a multiple sclerosis flare-up or relapse. In some aspects, the subject can have early stage MS, clinically isolated syndrome (CIS), radiological isolated syndrome (RIS) or any type or subtype of MS. In some aspects, the subject can be suspected of having or is at risk for developing MS or a MS relapse. In some aspects, the subject can be a human. In some aspects, the sample can be saliva. In some aspects, the subject can present with one or more symptoms of MS.

Methods of Treating

Disclosed herein are methods of treating a patient with multiple sclerosis (MS) or a MS-related disease. In some aspects, the method can comprise treating or preventing MS or a MS-related disease or a MS flare-up. In some aspects, the method can comprise administering to a subject a composition comprising a salivary microbiome altering agent that, when administered to the subject, increases the abundance of *Haemophilus*, *Campylobacter*, *Prevotella_2*, *Alloprevotella*, or *Lautropia* in the saliva. In some aspects, the administration of a salivary microbiome altering agent can be done e.g., via a bacterial composition given orally.

Disclosed herein are methods of treating a patient with multiple sclerosis (MS). In some aspects, the methods can comprise: administering to the patient with MS a salivary microbiome altering agent to reduce growth of *Gemella* or *Streptococcus* genus or species, to support growth of *Haemophilus*, *Campylobacter*, *Prevotella_2*, *Alloprevotella*, or *Lautropia* genus or species, an MS therapeutic agent, or a combination thereof to the subject, wherein the patient is identified as needing the MS a salivary microbiome altering agent, the MS therapeutic agent, or a combination thereof by obtaining a biological sample from the patient; and detecting in the biological sample an increased amount of a *Gemella* or *Streptococcus* genus or species of bacteria or a decreased amount of a *Haemophilus, Campylobacter, Prevotella_2, Alloprevotella*, or *Lautropia* genus species of bacteria relative to that of a biological sample obtained from a control subject.

In some aspects, the MS related disease can be neuromyelitis optics, acute disseminated encephalomyelitis or clinically isolated syndrome. In some aspects, the step of detecting can comprise detecting by microarray. In some aspects, the step of detecting can comprise detecting by ELISA. In some aspects, wherein the one or more microbes detected can be from the genus *Gemella, Streptococcus, Haemophilus, Campylobacter, Prevotella_2, Alloprevotella*, or *Lautropia*. In some aspects, the sample can be saliva.

In some aspects, the treatment or prevention of MS or an MS flare-up in a subject can be initiated before the diagnosis of MS based on results of the microbial analysis of the methods disclosed herein. The goal of the treatment is to slow the disease process or to even stop it, or even prevent MS.

In some aspects, the methods can comprise administering to the subject diagnosed with MS a salivary microbiome altering agent to support growth of *Haemophilus, Campylobacter, Prevotella_2, Alloprevotella*, or *Lautropia*. In some aspects, the subject can be identified as needing a salivary microbiome altering agent. In some aspects, the salivary microbiome can be modulated or altered by changes in lifestyle, including but not limited to modifying diet, increasing exercise, and reducing smoking and alcohol consumption. High carbohydrate diets can increase growth of several genera including but not limited to *Clostridium, Lachnospiraceae Lachnospiraceae*, and *Ruminococcaceae* and reduce growth of several genera including but not limited to *Bacteroides, Bifidobacteria*, and Enterobacteriaceas. High fat diets can increase growth of several genera including but not limited to *Alistipes, Bacteroides*, and *Bilophila*. High protein diets can increase growth of several genera including but not limited to *Roseburia, Eubacterium, Faecalbacterium, Lactobacilli*, and *Bacteroides*. High fiber diets can increase growth of bacteria that produce beneficial SCFAs. Low gluten diets can decrease growth of several genera including *Bifidobacteria, Prevotella*, and *Bacteroides*. Salivary microbiome altering agents can include but are not limited prebiotics to reduce oral biome dysbiosis, including arginine which is broken down by arginolytic species to generate ammonia which can increase growth of commensal beneficial streptococci species and reduce growth of damaging streptococci species (e.g., *S. mutans*); or succinic acid, beta-methyl-D-galactoside, or N-acetyl-D-mannosamine which promote growth of health associated bacteria genus and species. In some aspects, the salivary microbiome altering agent can be anti-microbial peptides (STAMPS) to kill specific genus or species.

In some aspects, the salivary microbiome altering agent can be specific short chain fatty acids (SCFAs) to replace endogenous beneficial SCFAs which are depleted by increased levels of bacterial genera or species which metabolize beneficial SCFAs; or due to reduced levels of bacterial genera or species which produce those beneficial SCFAs. In some aspects, the microbiome altering agent can be butyrate, butyric acid, iso-butyric acid, propionic acid, acetic acid, valeric acid, isovaleric acid, isocaproic acid, trimethylamine N-oxide, 3-hydroxybenzoic acid, 3,4-dihydroxybenzoic acid, dihydrocaffeic acid, indoxyl sulfate, or 4-ethylphenylsulfate.

In some aspects, the subject can be identified by: obtaining a biological sample from the subject, and detecting in the biological sample an increased abundance of a *Gemella* or *Streptococcus* genus or species of bacteria or a decreased abundance of a *Haemophilus, Campylobacter, Prevotella_2, Alloprevotella*, or *Lautropia* genus or species of bacteria relative to that of a biological sample obtained from a control subject.

In some aspects, the method can further comprise detecting the presence of one or more microbe-specific antibodies specific to one or more microbes disclosed herein. In some aspects, the method can further comprise determining the quantity of one or more of the microbe-specific antibodies in the sample. In some aspects, the method can further comprise amplifying one or more nucleic acid sequences in the sample. In some aspects, the one or more nucleic acid sequences can correspond to one or more of the microbes or taxa described herein.

In some aspects, the one or more nucleic acid sequences can be amplified using a primer pair that can specifically amplify the one or more nucleic acid sequences. In some aspects, the method can further comprise determining whether the expression of the one or more nucleic acid sequences corresponding to the one or more of the microbes or taxa described herein is overexpressed compared to expression levels of a nucleic acid sequence of the same one or more of the microbes or taxa described herein in a control. In some aspects, the method can further comprise determining whether the expression of the one or more nucleic acid sequences corresponding to the one or more of the microbes or taxa described herein is decreased compared to expression levels of a nucleic acid sequence of the same one or more of the microbes or taxa described herein in a control. In some aspects, the step of detecting can comprise detecting by hybridization reaction. In some aspects, the hybridization reaction can further comprise hybridizing the sample to one or more primer sets. In some aspects, the step of detecting can comprise detecting by a polymerase chain reaction.

Methods of Detection

The presence or absence or expression level of one or more microbes or microbe-specific antibodies disclosed herein can be determined directly (e.g., immunoassays, mass spectrometry) or indirectly (e.g., presence or absence of one or more antibodies that are specific to the one or more microbes or determining the mRNA expression of a protein or peptide). Examples of mass spectrometry include but are not limited to ionization sources such as EI, CI, MALDI, ESI, and analysis such as Quad, ion trap, TOF, FT or combinations thereof, spectrometry, isotope ratio mass spectrometry (IRMS), thermal ionization mass spectrometry (TIMS), spark source mass spectrometry, Multiple Reaction Monitoring (MRM) or SRM. Any of these techniques can be carried out in combination with prefractionation or enrichment methods. Examples of immunoassays include but are not limited to immunoblots, Western blots, Enzyme linked Immunosorbant Assay (ELISA), Enzyme immunoassay (EIA), radioimmune assay. Immunoassay methods use antibodies for detection and determination of levels of an antigen are known in the art. The antibody can be immobilized on a solid support such as a stick, plate, bead, microbead or array.

The presence or absence or expression level of one or more microbes or microbe-specific antibodies disclosed herein can be also be determined indirectly by determining the presence or absence of one or more antibodies that are specific to the one or more microbes in a tissue sample. RNA expression methods include but are not limited to extraction of cellular mRNA and Northern blotting using labeled probes that hybridize to transcripts encoding all or part of the gene, amplification of mRNA using gene-specific primers, polymerase chain reaction (PCR), and reverse transcriptase-polymerase chain reaction (RT-PCR), followed by quantitative detection of the gene product by a variety of methods; extraction of RNA from cells, followed by labeling, and then used to probe cDNA or olignonucleotides encoding the gene, in situ hybridization; and detection of a reporter gene.

Methods to measure protein expression levels include but are not limited to Western blot, immunoblot, ELISA, radio-immunoassay, immunoprecipitation, surface plasmon resonance, chemiluminescence, fluorescent polarization, phosphorescence, immunohistochemical analysis, microcytometry, microarray, microscopy, fluorescence activated cell sorting (FACS), and flow cytometry. The methods can also include specific protein property-based assays based including but not limited to enzymatic activity or interaction with other protein partners. Binding assays can also be used, and are well known in the art. For instance, a BIAcore machine can be used to determine the binding constant of a complex between two proteins. Other suitable assays for determining or detecting the binding of one protein to another include, immunoassays, such as ELISA and radioimmunoassays. Determining binding by monitoring the change in the spectroscopic can be used or optical properties of the proteins can be determined via fluorescence, UV absorption, circular dichroism, or nuclear magnetic resonance (NMR). Alternatively, immunoassays using specific antibody can be used to detect the expression on of a particular protein on a tumor cell.

As mentioned above, one of ordinary skill in the art can determine the presence of expression level of one or more microbes or microbe-specific antibodies (proteins or nucleic acids) disclosed herein any number of ways. To detect or quantify the level of RNA products of the biomarkers within a sample, arrays, such as microarrays, RT-PCR (including quantitative RT-PCR), nuclease protection assays and Northern blot analyses can be used. Accordingly, in some aspects, the expression levels of one or more of the microbes can be determined using arrays, microarrays, RT-PCR, quantitative RT-PCR, nuclease protection assays or Northern blot analyses.

An array is a form of solid support. An array detector is also a form of solid support to which multiple different capture compounds or detection compounds have been coupled in an array, grid, or other organized pattern.

Solid-state substrates for use in solid supports can include, for instance, any solid material to which molecules can be coupled. Examples of such materials include but are not limited to acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, poly lactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or any combination thereof. Solid-state substrates and solid supports can be porous or non-porous. An example of a solid-state substrate is a microtiter dish (e.g., a standard 96-well type). A multiwell glass slide can also be used. For example, such as one containing one array per well can be used, allowing for greater control of assay reproducibility, increased throughput and sample handling, and ease of automation.

Different compounds can be used together as a set. The set can be used as a mixture of all or subsets of the compounds (e.g., microbe-specific antibodies) used separately in separate reactions, or immobilized in an array. Compounds used separately or as mixtures can be physically separable through, for example, association with or immobilization on a solid support. An array can include a plurality of compounds immobilized at identified or predefined locations on the array. Each predefined location on the array can generally have one type of component (that is, all the components at that location are the same). Each location can have multiple copies of the component. The spatial separation of different components in the array allows separate detection and identification of the polynucleotides or polypeptides disclosed herein.

It is not required that a given array be a single unit or structure. The set of compounds can be distributed over any number of solid supports. For example, each compound can be immobilized in a separate reaction tube or container, or on separate beads or microparticles. Different aspects of the disclosed method and use of the or array or diagnostic device can be performed with different components (e.g., different compounds specific for different proteins) immobilized on a solid support.

Some solid supports can have capture compounds, such as antibodies, attached to a solid-state substrate. Such capture compounds can be specific for calcifying nanoparticles or a protein on calcifying nanoparticles. Captured calcified nanoparticles or proteins can then be detected by binding of a second detection compound, such as an antibody. The detection compound can be specific for the same or a different protein on the calcifying nanoparticle.

Methods for immobilizing nucleic acids, peptides or antibodies (and other proteins) to solid-state substrates are well established. Immobilization can be accomplished by attachment, for example, to aminated surfaces, carboxylated surfaces or hydroxylated surfaces using standard immobilization chemistries. Examples of attachment agents include but are not limited to cyanogen bromide, succinimide, aldehydes, tosyl chloride, avidinbiotin, photocrosslinkable agents, epoxides, maleimides and N-[y-Maleimidobutyryloxy] succinimide ester (GMBS), and a heterobifunctional crosslinker. Antibodies can be attached to a substrate by chemically cross-linking a free amino group on the antibody to reactive side groups present within the solid-state substrate. Antibodies can be, for example, chemically cross-linked to a substrate that contains free amino, carboxyl, or sulfur groups using glutaraldehyde, carbodiimides, or GMBS, respectively, as cross-linker agents. In this method, aqueous solutions containing free antibodies can be incubated with the solid-state substrate in the presence of glutaraldehyde or carbodiimide.

A method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate (BS3) or a heterobifunctional cross-linker agent such as GMBS. For cross-linking with GMBS, glass substrates can be chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides can be activated by immersing in a 0.5 mg/ml solution of GMBS in 1% dimethylformamide, 99% ethanol for 1 hour at room temperature. Antibodies or proteins can be added directly to the activated substrate, which can be blocked with solutions containing agents such as 2% bovine serum albumin, and air-dried. Other standard immobilization chemistries are known by those of ordinary skill in the art.

Each of the components (e.g., antibodies) immobilized on the solid support can be located in a different predefined region of the solid support. Each of the different predefined regions can be physically separated from each other. The distance between the different predefined regions of the solid support can be either fixed or variable. For example, in an array, each of the components can be arranged at fixed distances from each other, while components associated with beads will not be in a fixed spatial relationship. The use of multiple solid support units (e.g., multiple beads) can result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

In addition, the microbes described herein can also be used as markers (i.e., biomarkers) for susceptibility to or presence or progression of multiple sclerosis. The methods and assays described herein can be performed over time, and the change in the level of the markers assessed. For example, the assays can be performed every 24-72 hours for a period of 6 months to 1 year, and thereafter carried out as needed. Assays can also be completed prior to, during, or after a treatment protocol. Together, the microbes or microbe-specific antibodies disclosed herein can be used to profile an individual's risk or progression of multiple sclerosis. As used within this context, the terms "differentially expressed" or "differential expression" refers to difference in the level of expression of the biomarkers disclosed herein that can be assayed by measuring the level of expression of the products (e.g., RNA or gene product) of the biomarkers, such as the difference in level of messenger RNA transcript or a portion thereof expressed or of proteins expressed of the biomarkers. In some aspects, this difference is significantly different.

To improve sensitivity, more than one microbe disclosed herein can be assayed within a given sample. Binding agents specific for different proteins, antibodies, nucleic acids provided herein can be combined within a single assay. Further, multiple primers or probes can be used concurrently. To assist with such assays, specific biomarkers can assist in the specificity of such tests.

In general, disclosed herein are methods for the identification (including diagnosis) of microbes (e.g., microorganisms) in patients. There are a variety of methods used for identification of different microbes within the samples, e.g., providing specificity. In some aspects, a plurality of detection surfaces can be used. In some aspects, each detection surface can have a different specific microbe capture agents. That is, one detection surface may include microbe capture agents comprising antibodies to specific microbial species or genera, and another a different microbe capture agents to a different specific species. In some aspects, a plurality of detection surfaces can be used that are fluidically separated from one another; for example, a plurality of detection modules, for example detection channels, wherein one sample can be divided into the detection modules and can then be subjected to different conditions for evaluation. As outlined herein, the plurality of different detection surfaces can have non-specific, or specific microbe capture agents.

In some aspects, the detection surface(s) can rely on non-specific capture of the microbes or microbe-specific antibodies, but the detection method can rely on specific binding ligands; e.g., microbe-specific antibodies to a specific species or genera of microbe can be used with a fluorescent label. In some aspects, simultaneous detection usually relies on different binding ligands containing different labels, while sequential detection can be done using one or more washing steps followed by a different binding ligand with the same label. Another aspect of the invention avoids the use of either specific capture or specific labeling. In some aspects, the method provides for specific identification of a microbe using spatial separation of the microbes on the detection surface based on detectable or known changes. For example, the ability to detect the division of single microorganisms allows identification on the basis of any number of parameters, particularly kinetic parameters, including but not limited to growth rates, assessment of metabolic activity, rate of cell kill with different antibiotics, as well as microorganism morphology, which can include size, shape, and relationships to sibling organisms (e.g., growth into clusters or chains, two-dimensional growth on the surface or three-dimensional growth away from the surface). In addition to the evaluation of rates, single data point analysis may also be done (e.g., increased area associated with an individual microbes on the surface (e.g., positive growth), stagnant area (no positive growth) or loss of area (e.g., negative growth, apoptosis and/or death).

In some aspects, the invention provides a solid support or a kit for detecting multiple sclerosis in subject. In some aspects, the subject can be suspected of having or is at risk for having multiple sclerosis. In some aspects, the invention provides a solid support or a kit for detecting one or more antibodies in a sample. In some aspects, the detection of the presence of one or more microbe-specific antibodies can be indicative of multiple sclerosis. In some aspects, the invention provides a solid support or a kit for detecting one or more microbes in a sample. In some aspects, the sample can be from a subject at risk of developing or is suspected of having multiple sclerosis. The solid support or kit can include nucleic acid probes, antibodies, microbe-specific antibodies, primers, and/or microbe capture agents that can be useful for determining the presence of one or more microbes disclosed herein.

The disclosed methods also provide for the quantification and/or qualification of susceptibility of a desired treatment based on the identification (or absence of such identification) of one or more microbes. Said information can lead to therapeutic decisions.

Protein Arrays

Disclosed herein are polypeptide or protein arrays. In some aspects, the protein arrays can comprise primers or probes including antibodies, aptamers, and other cognate binding ligands specific to one or more of the microbes disclosed herein. Protein arrays and methods of constructing the protein arrays are well known to one of ordinary skill in the art.

One type of protein array that can be suitable uses an immobilized "capture antibody." The polypeptides are bound to a solid substrate (e.g., glass) with a treated surface (e.g., aminosilane) or through a biotin-streptavidin conjugation. The arrays are then incubated with a solution containing probe that can bind to the capture antibodies in a manner dependent upon time, buffer components, and recognition specificity. The probes can then be visualized directly if they have been previously labeled, or can be bound to a secondary labeled reagent (e.g., another antibody). The amount of probe bound to the capture antibody that is visualized can depend upon the labeling method utilized; generally, a CCD imager or laser scanner that uses filter sets that are appropriate to excite and detect the emissions of the label can be used. The imager converts the amount of detected photons into an electronic signal (often an 8-bit or 16-bit scale) that can be analyzed using commercially available software packages.

The substrate of the array can be organic or inorganic, biological or non-biological or any combination of these materials. The substrate can be transparent or translucent. Examples of materials suitable for use as a substrate in the array include but are not limited to silicon, silica, quartz, glass, controlled pore glass, carbon, alumina, titanium dioxide, germanium, silicon nitride, zeolites, and gallium arsenide; and metals including gold, platinum, aluminum, copper, titanium, and their alloys. Ceramics and polymers can also be used as substrates. Suitable polymers include, but are not limited to polystyrene; poly(tetra)fluorethylene; (poly)vinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PM I); polyalkenesulfone (PAS); polyhydroxyethylmethacrylate; polydimethylsiloxane; polyacrylamide; polyimide; co-block-polymers; and Eupergit®. Photoresists, polymerized Langmuir-Blodgett films, and LIGA structures can also serve as substrates.

The array can further comprise a coating that can be formed on the substrate or applied to the substrate. The substrate can be modified with a coating by using thin-film technology based on either physical vapor deposition (PVD) or plasma-enhanced chemical vapor deposition (PECVD). Alternatively, plasma exposure can be used to directly activate the substrate. For instance, plasma etch procedures can be used to oxidize a polymeric surface (i.e., polystyrene or polyethylene to expose polar functionalities such as hydroxyls, carboxylic acids, aldehydes and the like).

The coating can comprise a metal film. Examples of metal films include but are not limited to aluminum, chromium, titanium, nickel stainless steel zinc, lead, iron, magnesium, manganese, cadmium, tungsten, cobalt, and alloys or oxides thereof. In some aspects, the metal film can be a noble metal film. Examples of noble metals that can be used for a coating include, but are not limited to, gold, platinum, silver, copper, and palladium. In some aspects, the coating comprises gold or a gold alloy. Electron-beam evaporation can be used to provide a thin coating of gold on the surface. In some aspects, the metal film can be from about 50 nm to about 500 nm in thickness.

Alternatively, the coating can be silicon, silicon oxide, silicon nitride, silicon hydride, indium tin oxide, magnesium oxide, alumina, glass, hydroxylated surfaces, and a polymer.

The arrays described herein can comprise a collection of addressable elements. Such elements can be spatially addressable, such as arrays contained within microtiter plates or printed on planar surfaces wherein each element can be present at distinct X and Y coordinates. Alternatively, elements can be addressable based on tags, beads, nanoparticles, or physical properties. The microarrays can be prepared according to the methods known to one of ordinary skill in the art. The term "arrays" as used herein can refer to any biologic assay with multiple addressable elements. In some aspects, the addressable elements can be polypeptides (e.g., antibodies or fragments thereof) or nucleic acid probes. As used herein, "elements" refer to any probe (polypeptide or nucleic acid based) that can be bound by a one or more microbes disclosed herein, polypeptide fragment or transcript encoding such polypeptides, as related or associated with any of the microbes disclosed herein. Molecules can be, but are not limited to, proteins, polypeptides, peptides, RNA, DNA, lipids, glycosylated molecules, carbohydrates, polypeptides with phosphorylation modifications, and polypeptides with citrulline modifications, aptamers, oxidated molecules, and other molecules.

For the elements described herein, "addressability" refers to the location, position, tags, cleavable tags or markers, identifiers, spectral properties, electrophoretic properties, or other physical properties that enable identification of the element. An example of addressability, also known as coding, is spatial addressability, where the position of the molecule is fixed, and that position is correlated with the identity. This type of spatial array can generally be synthesized or spotted onto a planar substrate, producing, for example, microarrays, where a large number of different molecules are densely laid out in a small area (e.g., comprising at least about 400 different sequences per cm2, and can be 1000 sequences per $cm^2$ or as many as 5000 sequences per $cm^2$, or more). Less dense arrays (e.g., ELISA or RIA plates) where wells in a plate each contain a distinct probe can comprise from about 96 sequences per plate, up to about 100 sequences per $cm^2$, up to the density of a microarray. Other spatial arrays utilize fiber optics, where distinct probes can be bound to fibers, which can be formed into a bundle for binding and analysis. Methods for the manufacture and use of spatial arrays of polypeptides are known in the art.

An alternative to this type of spatial coding array is the use of molecular "tags," where the target probes can be attached to a detectable label, or tag, which can provide coded information about the sequence of the probe. These tags can be cleaved from the element, and subsequently detected to identify the element. In some aspects, a set of probes can be synthesized or attached to a set of coded beads, wherein each bead can be linked to a distinct probe, and wherein the beads can be coded in a manner that allows identification of the attached probe. In this type of "tag array," flow cytometry can be used for detection of binding. For example, microspheres having fluorescence coding and can identify a particular microsphere. The probe can be covalently bound to a "color coded" object. A labeled target polypeptide can be detected by flow cytometry, and the coding on the microsphere can be used to identify the bound probe (e.g., immunoglobulin, antigen binding fragments of immunoglobulins, or ligands).

In some aspects, the array can be an immunoglobulin (e.g., antibody or antigen-binding fragment thereof) array. As used herein, an "immunoglobulin array" refers to a spatially separated set of discrete molecular entities capable of binding to target polypeptides arranged in a manner that allows identification of the polypeptides contained within the sample. In some aspects, the array can comprise one or more of proteins, polypeptides, peptides, RNA, DNA, lipid, glycosylated molecules, polypeptides with phosphorylation modifications, and polypeptides with citrulline modifications, aptamers, and other molecules.

Compositions

Disclosed herein are compositions comprising one or more of the disclosed microbes or a salivary microbiome altering agent that, when administered to a subject, increases the abundance of *Haemophilus, Campylobacter, Prevotella_2, Alloprevotella,* or *Lautropia* genus or species or supports growth of these taxa in the saliva. Also disclosed herein are compositions comprising a salivary microbiome altering agent that, when administered to a subject, decreases the abundance of *Gemella* or *Streptococcus* genus or species or supports growth of these taxa in the saliva. In some aspects, the composition can comprise one or more of the disclosed microbes (alive or killed) and optionally a pharmaceutically acceptable carrier.

In some aspects, the compositions can be in the form of a food composition, pharmaceutical composition, nutraceutical, supplement or an anaerobical microbiota culture. It may include probiotics and other micro-organisms, prebiotics, antibiotics, growth factors, bacteriophages etc. The compositions can be administered mixed in food or drink, for example, or separately in the form of a tablets, capsules, microcapsules, powders, solutions, pastes, etc. Food composition can be any kind of food (functional, conventional and novel), food supplement, formula for nutritional purposes, or nutraceutical and it may contain any suitable additives and excipients. The effect of the bacterial supplementation can be enhanced by adding prebiotics such as fiber or oligosaccharides to the composition. The compositions can also be a prebiotic and optionally contain a pharmaceutically acceptable carrier. The compositions can contain live microbes of any of taxons disclosed herein and a prebioticial agent or compound supporting growth of these taxa and optionally a pharmaceutically acceptable carrier. In some aspects, the composition of the salivary microbiome can be changed by following a long term diet.

Disclosed herein are isolated antibodies, antibody fragments and antigen-binding fragments thereof, that can specifically bind to one or more of the microbes or microbe-specific antibodies disclosed herein. Optionally, the isolated antibodies, antibody fragments, or antigen-binding fragment thereof can be neutralizing antibodies.

As used herein, the term "antibodies" is used in a broad sense and includes both polyclonal and monoclonal antibodies. In addition to intact immunoglobulin molecules, also disclosed herein are antibody fragments or polymers of those immunoglobulin molecules, and human or humanized versions of immunoglobulin molecules or fragments thereof, as long as they are chosen for their ability to interact with the polypeptides disclosed herein. "Antibody fragments" are portions of a complete antibody. A complete antibody refers to an antibody having two complete light chains and two complete heavy chains. An antibody fragment lacks all or a portion of one or more of the chains. Examples of antibody fragments include, but are not limited to, half antibodies and fragments of half antibodies. A half antibody is composed of a single light chain and a single heavy chain. Half antibodies and half antibody fragments can be produced by reducing an antibody or antibody fragment having two light chains and two heavy chains. Such antibody fragments are referred to as reduced antibodies. Reduced antibodies have exposed and reactive sulfhydryl groups. These sulfhydryl groups can be used as reactive chemical groups or coupling of biomolecules to the antibody fragment. A preferred half antibody fragment is a F(ab). The hinge region of an antibody or antibody fragment is the region where the light chain ends and the heavy chain goes on.

Antibody fragments for use in the methods disclosed herein can bind antigens (e.g. microbe-specific antibodies or one or more of the microbes described herein). In some aspects, the antibody fragment can be specific for an antigen. An antibody or antibody fragment is specific for an antigen if it binds with significantly greater affinity to one epitope than to other epitopes. The antigen can be any molecule, compound, composition, or portion thereof to which an antibody fragment can bind. For example, the antigen can be a microbe-specific antibody or one or more of the microbes described herein. An analyte can be any molecule, compound or composition of interest. The antibodies or antibody fragments can be tested for their desired activity using the in vitro assays described herein, or by analogous methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. Also disclosed are "chimeric" antibodies in which a portion of the heavy or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851 6855 (1984)).

Monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent.

Monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, such as an Fv, Fab, Fab', or other antigen binding portion of an antibody, can be accomplished using routine techniques known in the art. For example, digestion can be performed using papain. Examples of papain digestion are described in WO 94/29348 published Dec. 22, 1994 and U.S. Pat. No. 4,342,566, the contents of which are hereby incorporated by reference in its entirety for its teaching of papain digestion of antibodies to prepare monovaltent antibodies. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

Fragments, whether attached to other sequences, can also include insertions, deletions, substitutions, or other selected modifications of particular regions or specific amino acid residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86 95, 1991). Human antibodies (and fragments thereof) can also be produced using phage display libraries (Hoogenboom et al., J. Mol. Biol., 227:381, 1991; Marks et al., J. Mol. Biol., 222:581, 1991).

Human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255 258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ line antibody gene array into such germ line mutant mice results in the production of human antibodies upon antigen challenge. Antibodies having the desired activity are selected using Env-CD4-co-receptor complexes as described herein.

Optionally, human antibodies can be made from memory B cells using a method for Epstein-Barr virus transformation of human B cells. (See, e.g., Triaggiai et al., An efficient method to make human monoclonal antibodies from memory B cells: potent neutralization of SARS coronavirus, Nat Med. 2004 August; 10(8):871-5. (2004)), which is herein incorporated by reference in its entirety for its teaching of a method to make human monoclonal antibodies from memory B cells). In short, memory B cells from a subject who has survived a natural infection are isolated and immortalized with EBV in the presence of irradiated mononuclear cells and a CpG oligonuleotide that acts as a polyclonal activator of memory B cells. The memory B cells are cultured and analyzed for the presence of specific antibodies. EBV-B cells from the culture producing the antibodies of the desired specificity are then cloned by limiting dilution in the presence of irradiated mononuclear cells, with the addition of CpG 2006 to increase cloning efficiency, and cultured. After culture of the EBV-B cells, monoclonal antibodies can be isolated. Such a method offers (1) antibodies that are produced by immortalization of memory B lymphocytes which are stable over a lifetime and can easily be isolated from peripheral blood and (2) the antibodies isolated from a primed natural host who has survived a natural infection, thus eliminating the need for immunization of experimental animals, which may show different susceptibility and, therefore, different immune responses.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323 327 (1988), and Presta, Curr. Opin. Struct. Biol., 2:593-596 (1992)).

Methods for humanizing non-human antibodies are well known in the art. For example, humanized antibodies can be generated according to the methods of Winter and coworkers (Jones et al., Nature, 321:522 525 (1986), Riechmann et al., Nature, 332:323-327 (1988), Verhoeyen et al., Science, 239:1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.). The antibodies disclosed herein can also be administered to a subject. Nucleic acid approaches for antibody delivery also exist. The broadly neutralizing antibodies to the polypeptides disclosed herein and antibody fragments can also be administered to subjects or subjects as a nucleic acid preparation (e.g., DNA or RNA) that encodes the antibody or antibody fragment, such that the subject's own cells take up the nucleic acid, and produce and secrete the encoded antibody or antibody fragment.

Kits

In some aspects, kits are disclosed for use in a methods for detection of one or more of the disclosed microbes. In some aspects, kits are disclosed for use in methods for detection and risk assessment of multiple sclerosis, comprising means for determining alterations in the microbiota, and in some aspects, salivary microbiota. The kits can comprise reagents and means for determining the abundance of one or more of the taxa disclosed herein in a sample In some aspects, the kits can include solid supports comprising one or more primers, probes, polypeptides, or antibodies capable of hybridizing or binding to one or more of the microbes described herein. Solid supports are solid state substrates or supports that molecules, such as analytes and analyte binding molecules, can be associated. Analytes (e.g., calcifying nano-particles and proteins) can be associated with solid supports directly or indirectly. For example, analytes can be directly immobilized on solid supports. Analyte capture agents (e.g., capture compounds) can also be immobilized on solid supports.

The kit can also comprise reagents that can be used for various auxiliary substances so that the kit can be used easily and efficiently, e.g., solvents, wash buffers etc.

EXAMPLES

Example 1: Deep DNA Metagenomic Sequencing Reveals Oral Microbiome Divergence Between Monozygotic Twins Discordant for Multiple Sclerosis Severity Abstract. In contrast to gut, the oral microbiome of MS patients has not been characterized. Deep sequencing of saliva DNA from a pair of monozygotic twins (MSF1 with relapsing remitting MS; MSF2 with clinically isolated syndrome) identified 2,036 bacterial species. Relative abundances of 3 phyla were higher, and 3 lower in MSF1 versus MSF2. Species diversity was greater in MSF2, and 20 abundant species differed at least 2-fold. Pathway analysis identified 116 functional hierarchies differing 50% or more. Although limited to one pair of twins, these data suggest that oral microbiome analysis may be useful for diagnosis or monitoring therapeutic efficacy.

The precise etiology of multiple sclerosis (MS) remains to be determined, however, recent progress in characterizing genetic diversity helps to distinguish genetic and environmental determinants. The first genetic factor identified for MS susceptibility was major histocompatibility locus HLA, with the main risk factor identified as HLA-DRB1*15:01, later found to be associated with earlier onset and faster conversion from clinically isolated syndrome (CIS) to definite MS (Isobe et al., JAMA neurology. 2016; 73:795-802). The first genetic variants associated with MS disease course were found by whole exome sequencing that located variants in 3 non-HLA genes (Gil-Varea et al., Journal of neuroinflammation. 2018; 15:265). More recent genome wide association studies (GWAS) (Beecham et al., Nature genetics. 2013; 45:1353-60; and George et al., Neurology Genetics. 2016; 2:e87) led to identification of hundreds of risk factors for MS, but each having a small effect on overall risk, and in total thought to account for up to 25% of total genetic inheritability (Patsopoulos, Genetics of Multiple Sclerosis: An Overview and New Directions. Cold Spring Harbor perspectives in medicine. 2018; 8).

In contrast to human genetic variants, it is now accepted that microorganism levels and diversity in human tissues are associated with disease progression and severity. Numerous factors induce changes in the microbiome including diet, social interactions, stress, and medications. Knowledge of microbiome structure could help guide therapeutic approaches to increase levels of beneficial taxa, while reducing levels of detrimental microorganisms. Differences in biomes could also help account for the fact that identical twins have about 30% concordance of MS (Kuusisto et al., European journal of neurology. 2008; 15:1106-10). Although fecal samples are most often used as a proxy for the gastrointestinal microbiome, saliva has a similar degree of microbial diversity, and the relative ease of obtaining samples has led to it being used to examine microflora changes in neurodegenerative diseases (Boaden et al., Gerodontology. 2017; 34:343-56; Liu et al., Journal of Alzheimer's disease: JAD. 2019; 72:633-40; Panza et al., Brain: a journal of neurology, 2019; 142:2905-29; and Singhrao and Olsen, Journal of oral microbiology. 2019; 11:1563405).

The oral microbiome of MS patients was investigated and how it differs between MS patients with different disease severity was determined. To minimize the contribution of human genetic differences, saliva was analyzed from a pair of identical twins discordant for MS disease severity cohabitating with similar diets, one with a diagnosis of CIS, the other with RRMS. The differences between twins at phyla, genera, and species levels are reported herein; similarities to the gut microbiota dysbiosis reported for MS patients are also discussed; and the pathways found enriched in either twin.

Material & Methods. Patients. Identical female twins MSF1 and MSF2 of Hispanic descent were identified at the UIC MS clinic. MSF1 was diagnosed at age 25 with relapsing remitting MS (RRMS) based on clinical, imaging, and laboratory data; MSF2 was diagnosed at age 26 with clinically isolated syndrome (CIS) based on clinical and MRI data. At the time of sample collection, both were 32 years-old, MSF1 had an expanded disability status scale (EDSS) score of 1.0 and MSF2 had an EDSS score of 0 according to the 2017 revised McDonald's criteria (Thompson et al., The Lancet Neurology, 2018; 17:162-73). Significant co-morbidities were uterine fibroids and ovarian cysts in both twins. Both twins self-reported to not taking any disease modifying therapies for at least 18 months before samples were collected, and neither reported any gum disease nor other oral disease. Short Tandem Repeat (STR) profiling (Promega Powerflex® Fusion Systems) carried out by the Molecular Pathology laboratory at UIC gave a random match probability of 2.3×10-33 across 24 loci, confirming monozygosity.

Samples. Saliva samples were collected from MSF1 (Omnigene-oral-501 kit, DNA Genotek, Ottawa, Canada) and MSF2 (Saliva kit RU49000, Norgen Biotek, Ontario, Canada). At the time DNA collection, both twins had been living together, sharing a similar life style, were following identical low-fat, vegetable-rich diets, and were off medication for 18 months. Neither were tobacco users nor had antibiotic exposure over the month before sample collection. Genomic DNA (gDNA) was extracted using QIAGEN Allprep kit (Cat #80204) per manufacturer's recommendations, quality determined using TapeStation2200, and quantified using a Qubit 2.0 (Invitrogen) fluorimeter. Samples were stored at −80° C. until use. Saliva samples (n=80) from a cohort of healthy individuals of Hispanic descent living in the Chicago area were collected, genomic DNA isolated, and microbial taxa determined by 16S rRNA sequencing as part of a larger study examining the diversity of the oral microbiome in dentate versus edentulous individuals (Gazdeck et al., Oral diseases, 2019; 25:911-8).

Whole Genome Sequencing. Whole Genome Sequencing was carried out by Novagene (Beijing, China). Libraries were prepared from 1 μg gDNA (Illumina Truseq Nano DNA HT Sample Preparation Kit) following manufacturer's recommendations. Briefly, gDNA samples were sheared by sonication to 350 bp, fragments endpolished, poly(A)-tailed and amplified by PCR. Paired-end 150 bp reads were sequenced on an Illumina HiSeq X System. High quality raw sequence reads provided a depth of 50× coverage for MSF1 and 54× for MSF2. Mapping was performed using the BWA-MEM assembler with soft clipping against the human reference genome version hg38 masked for low complexity regions. Resulting BAM files were cleaned of PCR duplicates using PICARD software.

Taxonomic profiling. Raw reads that were unmapped against reference genome hg38 were mapped to the NCBI no-redundant nucleotide (nrNT) database using Centrifuge (Kim et al. 2016. Genome Res. 26, 1721-1729). MSF1 had 28.5M unmapped read pairs out of 640M total, and MSF2 had 6.2M unmapped read pairs out of 722M total. Taxonomic annotations for each read were obtained using the least common ancestor algorithm (MEGAN), then summarized across all reads to create counts per taxon.

Functional profiling. Raw reads were mapped to the Swissprot protein database using DIAMOND (Buchfink et al., Nature methods, 2015; 12:59-60). Gene ortholog annotations were assigned using the consensus of aligned references and summarized across all reads to create counts per ortholog for each sample. Higher level summaries of orthologous functions were created using KEGG BRITE hierarchical annotations (Kanehisa et al., Nucleic acids research, 2017; 45:D353-d61).

Results. Unmapped read pairs from MSF1 and MSF2 were mapped to the NCBI non-redundant nucleotide (nrNT) database, which yielded 15.14M read pairs for a total of 2.32 Gbp for MSF1, and 2.83M read pairs for a total of 0.45 Gbp for MSF2. Based on this difference, for subsequent comparisons, MSF2 reads were normalized by a factor of 5.184. The majority of reads mapped to Bacteria (97.8%), with a small percentage mapping to Archaea (0.04%), Virus and Phage (0.2%), and Eurkaryota (2.0%). Mapping identified 8,033 different annotated taxa. This list was filtered to remove species annotations that were reflective of sample origin, rather than a curated species name—those containing 'clone', 'symbiont', 'uncultured', 'unidentified', 'other', 'sp.', or 'bacterium' were excluded, resulting in removal of 4,091 annotated taxa. These constituted a small percentage of total reads (1.51M reads, or 10% for MSF1; 2.27M reads, or 15% for MSF2), with 2 taxa having an abundance greater than 1%. The remaining 3,942 taxa were filtered for ones having <100 reads in both MSF1 and MSF2 which led to removal of 1,906 taxa (0.25% of all reads). The remaining taxa could be assigned to 35 different phyla, 64 classes, 145 orders, 308 family, 829 genera, and 2,036 species. There were 6 phyla which accounted for >98.7% of all sequences in either MSF1 or MSF1 (FIG. 1A). Of those, 3 (Firmicutes, Bacteroidetes, and Actinobacteria) were higher in MSF1 than in MSF2; while 3 (Proteobacteria, Fusobacteria, and Spirochaetes) were higher in MSF2 than in MSF1.

Of the 829 different genera identified, 645 were present in MSF1 with abundance>100, and 812 in MSF2 having >100 reads. Of those, 628 were shared, with 17 genera unique to MSF1 and 184 unique to MSF2. The unique genera were present at 0.01% or less abundance. In MSF1, 10 genera were present at 1% or greater abundance, which together comprised 91.1% of genera (FIG. 1B). In MSF2, 15 genera were present at 1% or greater, making up 88.7% of genera. Amongst those, 5 *Campylobacter, Rothia, Veillonella, Atopobium*, and unknown) were approximately 2-fold or more higher in MSF1 than MSF2, while 7 (*Aggregatibacter, Neisseria, Serratia, Treponema, Filifactor*, and *Capnocytophaga*) were 2-fold or more higher in MSF2. The distribution and evenness of genera is higher in MSF2 (Shannon H-value of 2.85; 43% of the maximum of 6.7) compared to MSF1 (Shannon H-value of 2.42; 37% of the maximum of 6.5).

Figure 1C:
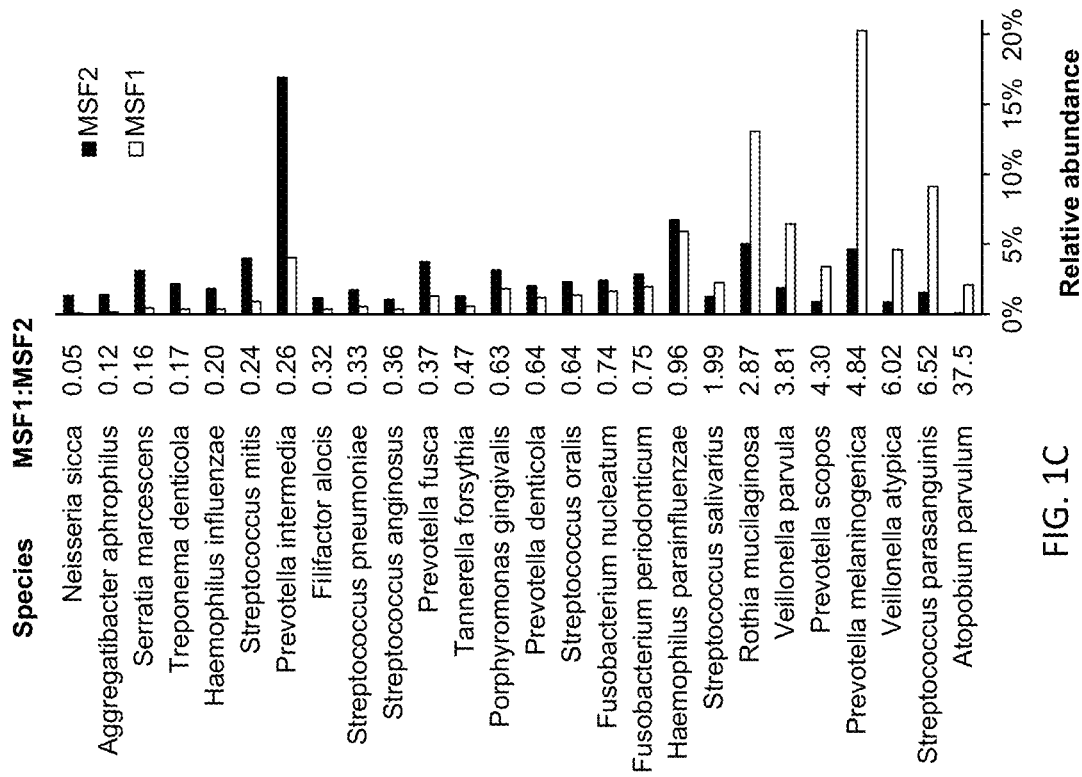

Overall species diversity was lower in MSF1 with 1,515 different species (>100 reads) compared to MSF2 having 1,975 different species (>100 reads). In MSF1, there were 17 species with a relative abundance of >1%, which together comprised 81% of sequences annotated to the species level. In MSF2, there were 23 species with a relative abundance of >1%, and together these taxa comprised 73% of sequences annotated to the level of species. Eight species were at least 2-fold higher in MSF1 versus MSF2 (FIG. 1C) and 12 were at least 2-fold higher in MSF2 than in MSF1. There were 1,454 species shared between MSF1 and MSF2, with 61 unique to MSF1 and 521 unique to MSF2 resulting in 8.5-fold more unique species in MSF2 (Table 1). The distribution and evenness of species represented in the Shannon H-value was 3.81 (57% of the maximum of 6.72) for MSF2 compared to 3.26 in MSF1 (49% of the maximum of 6.72).

TABLE 1

Genus and Species distribution in MSF1 and MSF2

|  |  | Total | Unique* | Unique MSF2:MSF1 | Shared | Shannon Diversity | Shannon Evenness |
| --- | --- | --- | --- | --- | --- | --- | --- |
| Genera | MSF1 | 645 | 17 |  | 628 | 2.42 | 0.37 |
|  | MSF2 | 812 | 184 | 10.8 |  | 2.85 | 0.43 |
| Species | MSF1 | 1,515 | 61 |  | 1,454 | 3.39 | 0.46 |
|  | MSF2 | 1,975 | 521 | 8.5 |  | 4.03 | 0.53 |

*Unique is as a taxa having less than 100 reads in one twin but not the other.

Figure 2A:
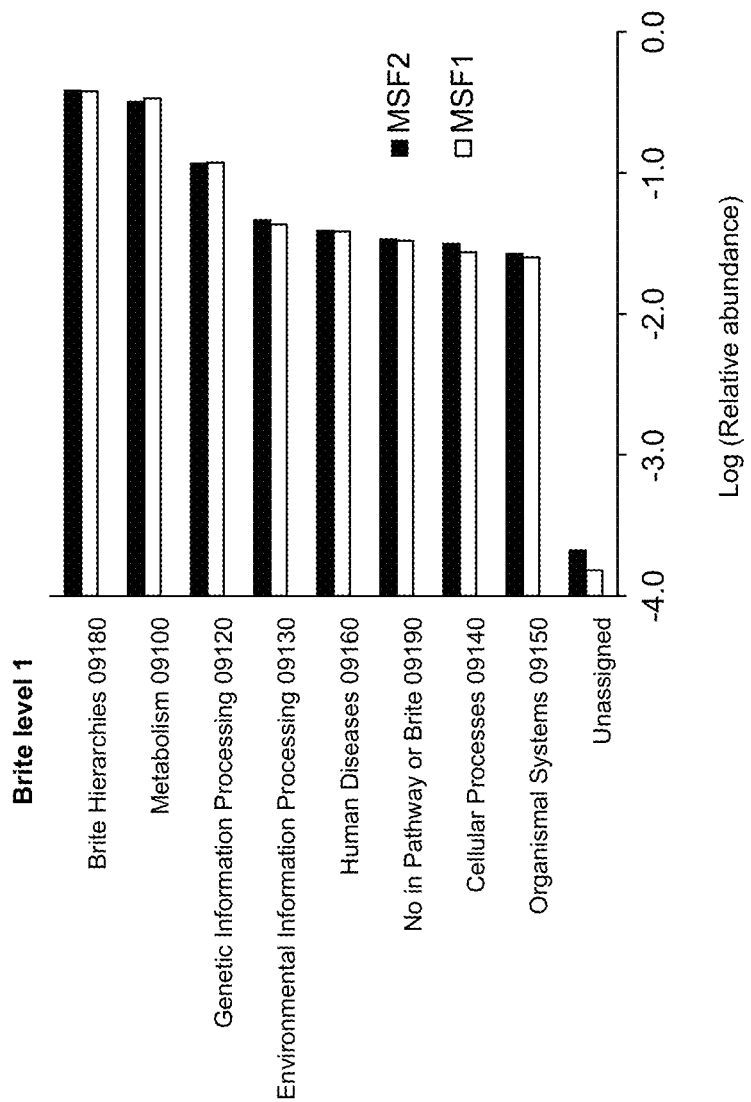
FIGS. 2A-C show pathway analysis of encoded proteins. Total reads for MSF1 and MSF2 were translated to proteins, then analyzed for KEGG BRITE hierarchical annotations.
Figure 2B:
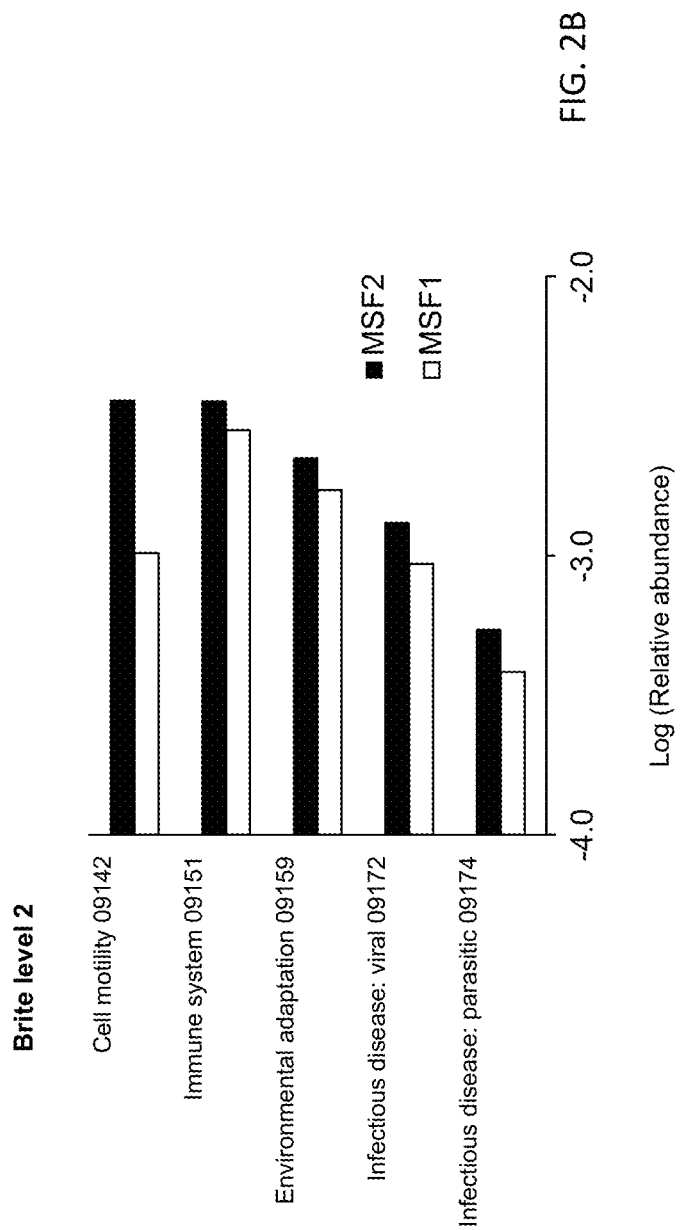
Figure 2C:
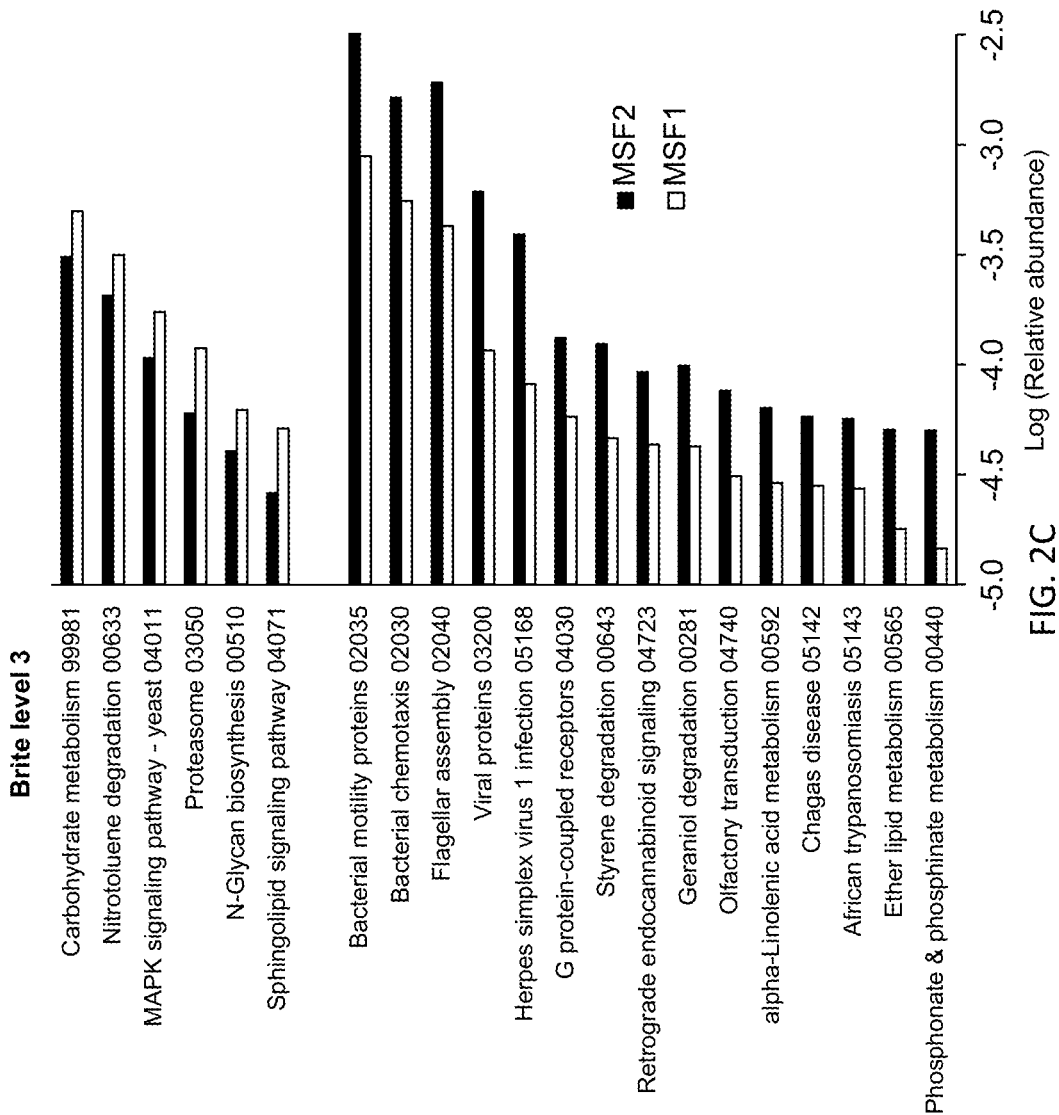

Pathway analysis identified 7 BRITE level 1 hierarchies present at roughly equal abundance in both patients (FIG. 2A). Differences between the twins could be observed upon classification into level 2 BRITE hierarchies, which identified 5 pathways present at 0.05% abundance or greater that differed by at least 20% between MSF1 and MSF2 (FIG. 2B). Classification into level 3 BRITE hierarchies identified 116 that differed by at least 50% between twins, of which 21 were present at 0.005% abundance or greater (FIG. 2C). Of those 15 features were present at higher relative abundance in MSF2 relative to MSF1, while 6 features were lower in MSF2. Features with the largest differences were related to proteasome function (2-fold higher in MSF1) and phosphonate and phosphinate metabolism (3-fold higher in MSF2).

The relative abundancies of the twins was compared to those determined in a cohort of healthy individuals (HCs) of Hispanic descent living in the Chicago area. At the phylum level the relative abundancies of bacteroidetes and proteobacteria were higher in both twins compared to the HCs, while levels of firmicutes and actinobacteria were lower. At the genus level, relative levels of *prevotella, rothia*, and *haemophilus* were higher in both twins compared to HCs, while levels of *streptococcus* and *actinomyces* were lower. In addition, Shannon alpha diversities of genera in the twins (2.42 and 2.85) are comparable to the Shannon diversity of the HCs (2.84±0.40, mean±sd).

Discussion Several studies have reported gut microbiome dysbiosis in MS patients compared to healthy controls, however, the results described herein represent a first characterization of the MS oral microbiome. Microbiota was evaluated in saliva samples from a pair of identical twins discordant for MS severity, where one (MSF2) had an ongoing CIS diagnosis 10 years after initial diagnosis, and the other (MSF1) a diagnosis of RRMS. At the time of DNA collection, the twins followed identical low-fat vegetable-rich diets, had no oral abscesses or mucosal lesions, and were off medication for 18 months. While small differences in relative microbiota abundance were apparent at higher taxonomic levels, for genera and species present at 1% abundance or greater, differences as large as 36-fold were observed. In contrast, a comparison of the gut microbiome analyzed using 16S rRNA gene amplicon sequencing in identical twins discordant for MS severity showed few differences (Berer et al., Proceedings of the National Academy of Sciences of the United States of America. 2017; 114:10719-24). In that study, 34 twin pairs were examined in which one of the twins was unaffected; however, no differences were found in genera richness or abundance. Differences were observed when patients were stratified for use of disease modifying therapies, with the relative abundance of *Akkermansia muciniphila* higher in untreated patients compared to healthy controls. In contrast, it was found that the relative abundance of *A. muciniphila* was about 2-fold higher in MSF2 versus MSF1 (0.0036% versus 0.0018%).

The approach of using whole genome sequencing (WGS) combined with alignment to the non-redundant nucleotide (nrNT) database identified 8,033 species or species-level taxonomic features. Filtering of that data to remove taxa with unclear annotations (clone, symbiont, uncultured, unidentified, other, sp., bacterium) and any species detected at <100 reads (equivalent to 0.001% abundance) resulted in 2,036 species, 829 distinct genera, and 35 distinct phyla. In contrast, the current human oral microbiome database (HOMD) (Escapa et al., mSystems, 2018; 3:e00187-18) contains 15 different phyla, 211 genera, and 771 species. Of the 2,026 species identified by shot-gun approach, 225 are listed in HOMD comprising 93.0% of all species; of the 829 genera 121 are in HOMD and comprise 95.8% of all genera, and of the 135 phyla 10 are in HOMD comprising 99.3% of all phyla. Re-analysis using genera and species found in HOMD (Table 1) yields lower Shannon diversities and higher evenness in both MSF1 and MSF2; however, both diversity and evenness remain higher in MSF2 than MSF1.

Several reasons can account for the large difference in the results compared to the HOMD data. First, alignment to the nrNT identifies taxa whose annotations are not clearly associated with a defined species, but instead with sample origin. Also, distinct annotations are in nrNT assigned to the same species, or to species at the strain level; and sequences for non-16S rRNA bacterial genes are detected in nrNT not yet assigned to well annotated species and hence are not listed in HOMD. These differences are also consistent with a study in which 16S rRNA amplicon sequencing was directly compared to deep WGS using the same fecal sample (Ranjan et al., biochemical and biophysical research communications, 2016; 469:967-77), and which showed that WGS identified approximately twice as many species as the 16S method; and overall diversity was much greater. Identification of about 2,000 species in the current study is therefore in line with their finding of over 4,000 species in the fecal microbiome by WGS.

A comparison of differences between MSF1 and MSF2 to differences reported between gut microbiomes of MS patients and healthy controls (HC), or between patients with active versus non-active disease shows some similarities (Table 2). At the phylum level, Actinobacteria and Proteobacteria were decreased (Chen et al., Scientific reports. 2016; 6:28484) in the gut biome of RRMS patients with active disease compared to HCs; in the current study Proteobacteria was lower, although Actinobacteria was higher in MSF1. Several genera and species were present at lower levels in the gut microbiome of MS patients compared to HCs, and lower levels of some of these were also seen comparing MSF1 to MSF2. While this suggests that a subset of relative abundance changes in oral taxa may parallel changes in the gut, a few studies have directly compared oral to gut (using fecal samples) microbiomes, and show that these microbiomes are highly distinct, with weak correlations observed (Lokmer et al., Scientific reports, 2020; 10:2856, Russo et al., Frontiers in microbiology, 2017; 8:2699, and Stewart et al., Peer J. 2018; 6:e4693).

TABLE 2

| Taxa differences shared in gut and oral microbiomes | | | |
|---|---|---|---|
| Taxa Level | MSF1:MSF2 | MS:HC | Reference |
| Phylum | | | |
| Proteobacteria | Down | Down | (Chen et al., 2016) |
| Genus | | | |
| *Anaerostipes* | Down | Down | (Miyake et al., 2015) |
| *Faecalibacterium* | Down | Down | (Miyake et al., 2015) |
| *Slackia* | Down | Down | (Jangi et al., 2016) |
| *Haemophilus* | Down | Down | (Chen et al., 2016) |
| *Lactobacillus* | Down | Down | (Chen et al., 2016) |
| Parabacteroides | Down | Down | (Chen et al., 2016) |

TABLE 2-continued

Taxa differences shared in gut and oral microbiomes

| Taxa Level | MSF1:MSF2 | MS:HC | Reference |
| --- | --- | --- | --- |
| *Atopobium* | Up | Up | (Trendett et al., 2016) |
| *Bifidobacterium* | Up | Up | (Trendett et al., 2016) |
| *Megamonas* | Up | Up | (Trendett et al., 2016) |
| *Megasphaera* | Up | Up | (Trendett et al., 2016) |
| *Prevotella* | Up | Up | (Trendett et al., 2016) |
| Species | | | |
| *[Eubacterium] rectale* | Down | Down | (Miyake et al., 2015) |
| *Anaerostipes hadrus* | Down | Down | (Miyake et al., 2015) |
| *Prevotella stercorea* | Down | Down | (Jangi et al., 2016) |
| *Faecalibacterium prausnitzii* | Down | Down | (Trendett et al., 2016) |
| *Eggerthella lenta* | Up | Up | (Miyake et al., 2015) |
| *Streptococcus thermophilus* | Up | Up | (Miyake et al., 2015) |

In humans, two phyla dominate in the gut: Firmicutes (associated with a Western, carnivore diet) and Bacteroidetes (associated with a vegetarian and omnivore diet). MS patients with greater disease activity have a higher ratio of Firmicutes to Bacteroidetes in the gut (Cosorich et al., Science advances, 2017; 3:e1700492). It was also reported that RRMS patients have increased Actinobacteria; and decreased *Bacteroides* compared to healthy controls (Furusawa et al., Seminars in immunopathology, 2015; 37:17-25); and that levels of *Bacteroides* were inversely correlated with Treg numbers in MS patients, while Fusobacteria correlated with Tregs in healthy controls (Tremlett et al., BMC neurology, 2016; 16:182). Consistent with these findings, in MSF2, the relative level of Firmicutes to *Bacteroides* (24.9% versus 37.5%) is less than in MSF1 (35.4% versus 40.0%); levels of Actinobacteria were higher in MSF1 than MSF2 (7.7% versus 5.3%); and levels of Fusobacteria were lower in MSF1 than MSF2 (4.6% versus 7.0%). Correlation of these differences with MS disease may be due in part to reduced bacterial production of metabolites such as short chain fatty acids (SCFAs, primarily due to *Bacteroides*) which have well-characterized anti-inflammatory effects and can promote regulatory T cell numbers and function (Furusawa, et al., Seminars in immunopathology, 2015; 37:17-25; Melbye et al., Acta neurologica *Scandinavica*, 2019; 139: 208-19; and Smith et al., Science (New York, NY), 2013; 341:569-73). In this regard, it was reported that in RRMS patients (Jangi et al., Oncotarget. 2017; 8:71038-53), the relative abundance of several bacterial genus involved in the metabolism of the SCFA butyrate were lower as compared to healthy controls. Butyrate is a bacterial-derived metabolite that can increase the population of regulatory T cells (Furusawa, et al., Seminars in immunopathology, 2015; 37:17-25), which suppress Th1 Tcell activation and production of inflammatory factors. Inspection of the data shows 11 different bacterial species associated with butyrate metabolism, each 1.5 to 3-fold higher in MSF2 than in MSF1.

Amongst the most abundant species in both MSF1 and MSF2 is *Porphyromonas gingivalis* (*P. gingivalis*), which accounted for 1.8% of the species in MSF1 and 3.1% in MSF2. This is in contrast with abundance levels reported in 16s rRNA analysis of salivary samples from HCs of 0.0036% (Damgaard et al., Journal of oral microbiology, 2019; 11:1653123) and 0.09% (Chen et al., Frontiers in microbiology, 2019; 10:1723), this difference may be due in part to the method of measurement (shot-gun versus 16s RNA amplicon sequencing). *P. gingivalis* is an established biomarker for periodontitis (Szafranski et al., Applied and environmental microbiology, 2015; 81:1047-58), and produces proinflammatory serine dipeptide lipids, and lipopolysaccharide-G which can activate cytokine production from monocytes (Ballerini et al., Cytokine, 2017; 96:261-72). Moreover, both oral infection and subcutaneous injection with *P. gingivalis* worsened EAE (Polak et al., Journal of periodontology, 2018; 89:1461-6; and Shapira et al., Journal of periodontology. 2002; 73:511-6). These data suggest that *P. gingivalis* in the oral cavity may contribute to inflammatory activation in these patients.

Functional analysis identified several BRITE hierarchies which target a specific metabolite, or metabolite class. This includes pathways involved in phosphonate, ether lipids, alpha-linolenic acid, and geraniol metabolism. Although these were present at relatively low abundance (from 0.005% to 0.01%), they were present at 2.5 or greater abundance in MSF2 than MSF1. These have been suggested to play protective roles in EAE or to reduce inflammatory responses. The ether phospholipid edelfosine reduces EAE disease (Abramowski et al., Journal of neuroimmunology, 2014b; 274:111-24; and Chabannes et al., Journal of autoimmunity, 1992; 5: 199-211) and T cell activation (Abramowski et al., PloS one, 2014a; 9:e91970). Linolenic acid delays onset and severity in EAE (Adkins et al., 2019) and is associated with lower MS risk (Bjornevik et al., Multiple sclerosis (Houndmills, Basingstoke, England), 2017; 23:1830-8; and Bjornevik et al., Multiple sclerosis (Houndmills, Basingstoke, England), 2019; 25:987-93). Geraniol has anti-inflammatory properties (Huang et al., Drug design, development and therapy, 2018; 12:2897-903; and Jiang et al., Oncotarget. 2017; 8:71038-53). Bisphosphonates have been tested for efficacy in a variety of neurological diseases acting through inhibition of mevalonate pathways; inhibition of isoprenoid synthesis; and regulation of cholesterol synthesis (Zameer et al., Pharmacological reports: PR, 2018; 70:900-7). Two other pathways at higher levels in MSF2 are African trypanosomiasis and Chagas disease. Mice with *Trypanosoma bruci* infection developed less severe and delayed EAE (Wallberg and Harris, International immunology. 2005; 17:721-8), while infection with *Trypanosoma cruzi* led to immunosuppression and reduced EAE (Tadokoro et al., Journal of autoimmunity, 2004; 23:103-15). In contrast, the metabolite pathway enriched in MSF1 was nitrotoluene degradation, a chemical used in manufacture of pigments, photographic chemicals, and agricultural chemicals. As there are no reports of nitrotoluene in EAE or MS, it is not known if alterations in genes involved in its degradation could influence disease.

Comparison of relative taxa abundancies in MSF1 and MSF2 to HCs shows several differences. While these may reflect the limited nature of the current study, increased levels of proteobacteria (Qiao et al., Scientific reports, 2018; 8:1597) and bacteroidetes, and reduced levels of firmicutes were also been found when comparing the saliva microbiome of patients with autism to HCs (Kong et al., Nutrients. 2019; 11); and differences at the genus level when comparing the buccal microbiome of Parkinson's disease patients to HCs (Pereira et al., Parkinsonism & related disorders, 2017; 38:61-7).

In summary, comparison of the oral microbiome in saliva samples from monozygotic twins discordant for MS severity revealed differences at all taxonomic levels assessed. Several are consistent with ones reported in the gut microbiome between MS patients and HCs, or patients with active versus inactive disease. This may reflect displaced gut bacteria present at low levels in saliva or bacteria that reside on oral surfaces in addition to the gut. Although the salivary biome of monozygotic twins living under similar conditions including diet and overall health status was characterized, other environmental influences likely contribute to the differences observed (Gomez and Nelson, Microbial ecology, 2017; 73:492-503) and it has been reported that environment is the dominant factor that dictates the oral microbiome rather than host genetics (Shaw et al., mBio. 2017; 8).

Example 2: Comparison of Oral Microbiome Divergence Between Multiple Sclerosis Patients and Normal Controls Genomic DNA (gDNA) samples were isolated from saliva samples of 12 MS (2 SPMS, 8 RRMS, and 2 PPMS) patients, and 24 healthy controls (HC). The samples were then analyzed by 16S rRNA amplicon sequencing. In brief, libraries were prepared, then used for Illumina MiniSeq 150 bp paired-end sequencing. Raw data were merged, sequences trimmed to remove low quality reads, then adapters removed, and reads that lacked adapters, ambiguous nucleotides at ends, and reads with ambiguous internal reads discarded. PCR artefacts were removed using a standard checking program compared to a reference sequence database. Read counts were reduced using amplicon denoising to remove sequence clustering or dereplication. Taxonomic annotation was determined using a naïve Bayesian approach. Filters were used to remove specific taxa (e.g., mitochondrial, chloroplast), and finally read counts were normalized as the fraction of total counts in each sample.

Comparisons were made between the 12 MS and the 24 HC samples using non-parametric Mann Whitney tests; or parametric T-test when data were normally distributed.

Figure 3:
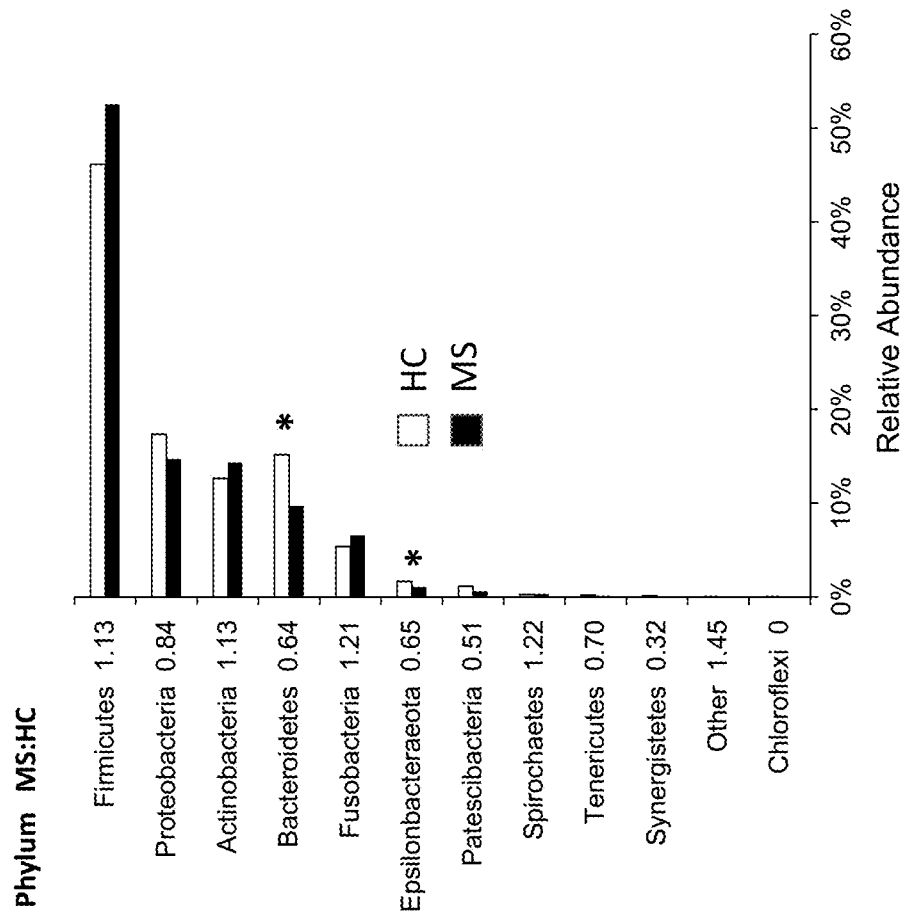
FIG. 3 shows the relative abundance of bacterial Phyla in MS patients and healthy controls (HC). *, P<0.05, Mann Whitney U test.

At the phylum level, 11 phyla were detected in both groups at a relative abundance of >0.005%, and a 12th (chloroflexi) in the HC samples at low abundance (0.001%) and in 2 of the 24 samples. The relative abundances (FIG. 3) were similar for MS and HC, with significantly ($P<0.05$) lower abundances in the MS patients detected for Bacteroidetes (MS: 9.7±4.0; HC: 15.1±6.5%, mean±SD) and Epsilonbacteraeota (MS: 1.1±0.9; HC: 1.7±1.0%). Receiver operator characteristic (ROC) curves for these 2 phyla (FIG. 4) show that both had good ability to distinguish between MS patients and HCs.

At the genus level, 126 different genera were detected in the MS patients, and 163 in the HCs. Ten genera were detected in the MS samples (Table 3A), and 47 present in the HC samples (Table 3B). The relative abundance of these were low, being less than 0.01% except for 5 in the HC group with abundancies between 0.011% (Neisseriaceae) and 0.037% (Veillonellaceae). Comparison of the MS to the HC cohorts (FIG. 5) shows that *Gemella* was significantly increased, while *Prevotella_2, Lautropia, Campylobacter*, and *Haemphilus* were significantly reduced in MS compared to the HC groups, and *Alloprevotella* almost significantly reduced ($P<0.06$). In addition, *Streptococcus* was significantly increased in the MS group if the 2 PPMS patient's data were excluded from the comparison.

TABLE 3A

Genera Unique to MS patients (n = 12 total)

| Genus | Relative Abundance | # in MS |
|---|---|---|
| *Parascardovia* | 0.0077% | 3 |
| Other | 0.0054% | 2 |
| *Propionibacterium* | 0.0034% | 2 |
| Other | 0.0082% | 1 |
| Other | 0.0067% | 1 |
| Other | 0.0065% | 1 |
| *Streptobacillus* | 0.0026% | 1 |
| *Ezakiella* | 0.0022% | 1 |
| Other | 0.0011% | 1 |
| *Sediminispirochaeta* | 0.0004% | 1 |

TABLE 3B

Genera unique to healthy controls (n = 24 total)

| Genus | Relative Abundance | # in HC |
|---|---|---|
| Other | 0.0134% | 7 |
| *Centipeda* | 0.0370% | 4 |
| *Conchiformibius* | 0.0107% | 4 |
| *Propionivibrio* | 0.0028% | 4 |
| Other | 0.0055% | 3 |
| *Simonsiella* | 0.0221% | 2 |
| Other | 0.0030% | 2 |
| *Acinetobacter* | 0.0026% | 2 |
| DNF00809 | 0.0019% | 2 |
| Family_XIII_AD3011_group | 0.0017% | 2 |
| *Desulfovibrio* | 0.0016% | 2 |
| W5053 | 0.0009% | 2 |
| *Flexilinea* | 0.0006% | 2 |
| *Sneathia* | 0.0138% | 1 |
| *Chryseobacterium* | 0.0091% | 1 |
| Other | 0.0034% | 1 |
| *Mannheimia* | 0.0030% | 1 |
| *Faecalibacterium* | 0.0028% | 1 |
| *Paracoccus* | 0.0027% | 1 |
| *Ottowia* | 0.0019% | 1 |
| *Prevotellaceae_YAB2003_group* | 0.0017% | 1 |
| *Blautia* | 0.0014% | 1 |
| *Bacillus* | 0.0014% | 1 |
| *Erysipelotrichaceae_UCG-004* | 0.0013% | 1 |
| Other | 0.0013% | 1 |
| *Pyramidobacter* | 0.0010% | 1 |
| *Tsukamurella* | 0.0010% | 1 |
| *Allorhizobium* | 0.0010% | 1 |
| Other | 0.0010% | 1 |
| *Ruminococcus_2* | 0.0007% | 1 |
| *Fastidiosipila* | 0.0006% | 1 |
| *Pseudomonas* | 0.0006% | 1 |
| *Agathobacter* | 0.0006% | 1 |
| *Kocuria* | 0.0006% | 1 |
| *Anaerostipes* | 0.0005% | 1 |
| *Pantoea* | 0.0004% | 1 |
| *Lachnospiraceae_ND3007_group* | 0.0004% | 1 |
| *Sphingopyxis* | 0.0004% | 1 |
| *Finegoldia* | 0.0004% | 1 |
| *Corynebacterium_1* | 0.0004% | 1 |
| *Lachnospiraceae_NK3A20_group* | 0.0003% | 1 |
| Other | 0.0003% | 1 |
| *Sphingomonas* | 0.0003% | 1 |
| *Acidaminococcus* | 0.0002% | 1 |

TABLE 3B-continued

Genera unique to healthy controls (n = 24 total)

| Genus | Relative Abundance | # in HC |
|---|---|---|
| Other | 0.0002% | 1 |
| Enhydrobacter | 0.0002% | 1 |
| Anaerococcus | 0.0002% | 1 |

Figures 6A, 6B:
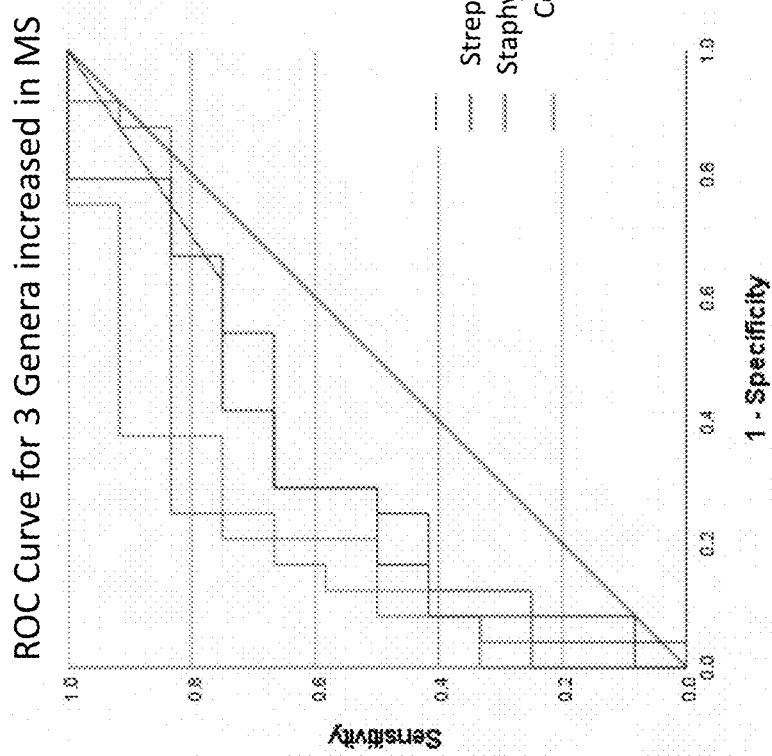
FIGS. 6A-B show receiver operator characteristic (ROC) curve showing sensitivity and 1-specificity for detection of MS patients versus HCs for genus *Gemella* which is increased in MS versus HC (FIG. 6A). AUC, area under the curve.
Figures 7A, 7B:
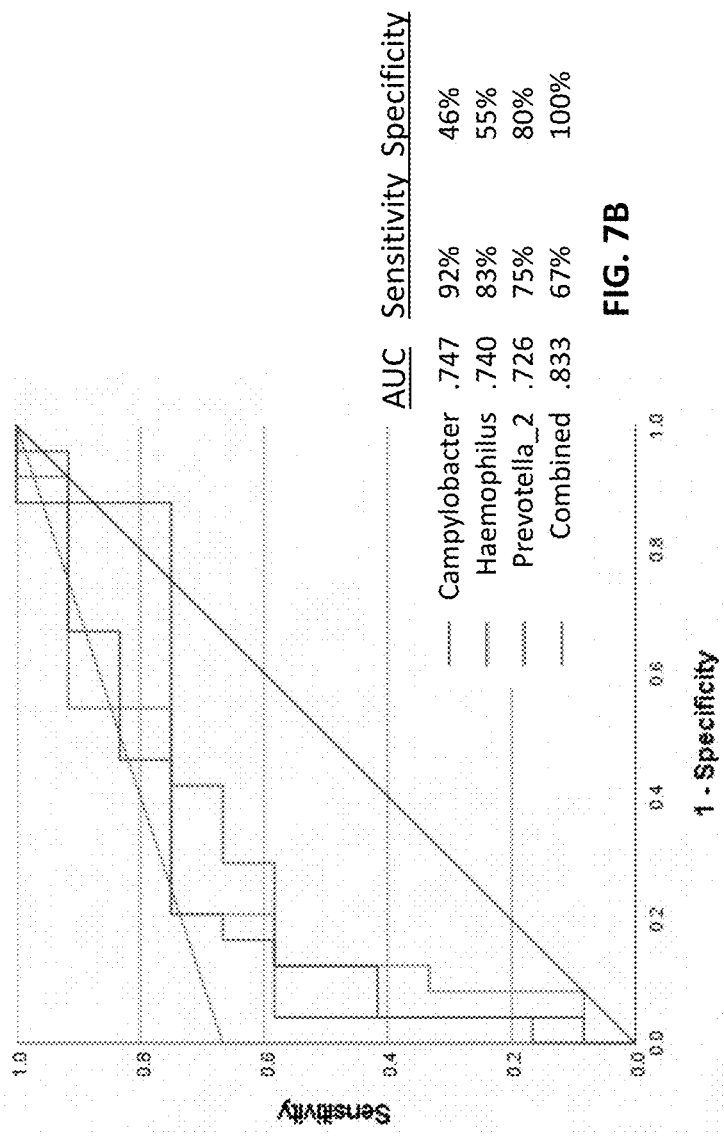
FIGS. 7A-B show receiver operator characteristic (ROC) curve showing sensitivity and 1-specificity for detection of MS patients versus HCs for 3 genera which are decreased in MS versus HC; and for the combination of the 3 genera determined by logistic regression and group membership (FIG. 7A). AUC, area under the curve.

FIG. 6 shows ROC curves for 3 genera that are increased in MS compared to HCs. While *Gemella, Streptococcus*, and *Staphyloccus* each had good ability to distinguish MS from HCs, the combinated ROC curve has a greater area under the curve (AUC, 0.816) and improved sensitivity (92%%, detecting 11 of the 12 MS patients) and good specificity (63%, mis-classifying 9 of the 24 HCs). FIG. 7 shows ROC curves for 3 genera that are decreased in MS compared to HCs, and the combined curve which has a better AUC (0.833), good sensitivity (67%, detecting 8 or the 12 MS patients), and perfect specificity (no mis-classifications of HC patients).

At the species level, 226 different genera were detected in the MS patients, and 307 in the HCs. Eighteen species detected in MS patients (Table 4A), and 81 species detected in the HC samples (Table 4B). Of the unique species in MS samples, one (e.g., *Actinomyces israelii*) was detected at 0.05 relative abundance and present in 5 of the 12 samples. In the HC group, the relative abundance of 21 was >0.01%, with the highest being *Neisseria flavescens* present at 0.93% but detected in 6 of the 24 samples.

TABLE 4A

Species Unique to MS patients (n = 12 total)

| Genus | Species | # in HV | Relative Abundance |
|---|---|---|---|
| Streptococcus | oralis | 1 | 0.0534% |
| Actinomyces | israelii | 5 | 0.0529% |
| Veillonella | atypica | 1 | 0.0128% |
| Other | Other | 1 | 0.0070% |
| Actinomyces | meyeri | 1 | 0.0061% |
| Scardovia | Other | 1 | 0.0061% |
| Other | Other | 1 | 0.0057% |
| Other | Other | 1 | 0.0056% |
| Parascardovia | denticolens | 2 | 0.0054% |
| Other | Other | 2 | 0.0046% |
| Prevotella_7 | multisaccharivorax | 1 | 0.0042% |
| Lactobacillus | gastricus | 1 | 0.0029% |
| Propionibacterium | acidifaciens | 2 | 0.0029% |
| Streptobacillus | Other | 1 | 0.0027% |
| Ezakiella | Other | 1 | 0.0019% |
| Parascardovia | Other | 1 | 0.0012% |
| Other | Other | 1 | 0.0010% |
| Sediminispirochaeta | Other | 1 | 0.0003% |

TABLE 4B

Species unique to healthy controls (n = 24 total)

| Genus | Species | # in HC | Relative Abundance |
|---|---|---|---|
| Neisseria | flavescens | 6 | 0.9257% |
| Aggregatibacter | Other | 2 | 0.0395% |
| Neisseria | mucosa | 1 | 0.0376% |
| Centipeda | Other | 4 | 0.0370% |
| Megasphaera | Other | 1 | 0.0299% |
| Treponema_2 | vincentii | 10 | 0.0163% |
| Sneathia | Other | 1 | 0.0138% |
| Other | Other | 7 | 0.0134% |
| Simonsiella | muelleri | 2 | 0.0123% |
| Prevotella_6 | Other | 4 | 0.0123% |
| Eikenella | Other | 3 | 0.0120% |
| Parvimonas | Other | 3 | 0.0118% |
| Conchiformibius | Other | 4 | 0.0107% |
| Simonsiella | Other | 1 | 0.0098% |
| Chryseobacterium | Other | 1 | 0.0091% |
| Mycoplasma | salivarium | 4 | 0.0090% |
| Aggregatibacter | actinomycetemcomitans | 2 | 0.0082% |
| Lactobacillus | oris | 1 | 0.0081% |
| Lachnoanaerobaculum | saburreum | 1 | 0.0078% |
| Actinomyces | cardiffensis | 2 | 0.0067% |
| Other | Other | 3 | 0.0055% |
| Atopobium | vaginae | 1 | 0.0044% |
| Actinomyces | timonensis | 2 | 0.0043% |
| Lachnoanaerobaculum | umeaense | 1 | 0.0042% |
| Campylobacter | curvus | 1 | 0.0037% |
| Other | Other | 1 | 0.0034% |
| Haemophilus | haemolyticus | 1 | 0.0033% |
| Abiotrophia | Other | 2 | 0.0030% |
| Other | Other | 2 | 0.0030% |
| Mannheimia | Other | 1 | 0.0030% |
| Faecalibacterium | Other | 1 | 0.0028% |
| Prevotella_7 | enoeca | 2 | 0.0028% |
| Propioni vibrio | Other | 4 | 0.0028% |
| Phocaeicola | Other | 1 | 0.0028% |
| Paracoccus | Other | 1 | 0.0027% |
| Prevotella_2 | marshii | 2 | 0.0027% |
| Acinetobacter | Other | 2 | 0.0026% |
| Porphyromonas | uenonis | 1 | 0.0021% |
| Rodentibacter | Other | 2 | 0.0020% |
| DNF00809 | Other | 2 | 0.0019% |

TABLE 4B-continued

Species unique to healthy controls (n = 24 total)

| Genus | Species | # in HC | Relative Abundance |
|---|---|---|---|
| Ottowia | Other | 1 | 0.0019% |
| Prevotellaceae_YAB2003_group | Other | 1 | 0.0017% |
| Family_XIII_AD3011_group | Other | 2 | 0.0017% |
| Prevotella | timonensis | 1 | 0.0016% |
| Desulfovibrio | Other | 2 | 0.0016% |
| Blautia | Other | 1 | 0.0014% |
| Bacillus | Other | 1 | 0.0014% |
| Erysipelotrichaceae_UCG-004 | Other | 1 | 0.0013% |
| Other | Other | 1 | 0.0013% |
| Pyramidobacter | piscolens | 1 | 0.0010% |
| Treponema_2 | amylovorum | 1 | 0.0010% |
| Allorhizobium | Other | 1 | 0.0010% |
| Tsukamurella | Other | 1 | 0.0010% |
| Other | Other | 1 | 0.0010% |
| Corynebacterium | Other | 1 | 0.0009% |
| W5053 | Other | 2 | 0.0009% |
| Treponema_2 | pectinovorum | 1 | 0.0008% |
| Prevotella_7 | pleuritidis | 1 | 0.0007% |
| Ruminococcus_2 | bromii | 1 | 0.0007% |
| Capnocytophaga | haemolytica | 2 | 0.0007% |
| Fastidiosipila | Other | 1 | 0.0006% |
| Pseudomonas | Other | 1 | 0.0006% |
| Flexilinea | Other | 2 | 0.0006% |
| Agathobacter | Other | 1 | 0.0006% |
| Kocuria | Other | 1 | 0.0006% |
| Anaerostipes | hadrus | 1 | 0.0005% |
| Bacteroides | vulgatus | 1 | 0.0005% |
| Prevotella | disiens | 1 | 0.0005% |
| Pantoea | Other | 1 | 0.0004% |
| Lachnospiraceae_ND3007_group | Other | 1 | 0.0004% |
| Sphingopyxis | Other | 1 | 0.0004% |
| Finegoldia | magna | 1 | 0.0004% |
| Corynebacterium_1 | Other | 1 | 0.0004% |
| Lachnospiraceae_NK3A20_group | Other | 1 | 0.0003% |
| Other | Other | 1 | 0.0003% |
| Sphingomonas | Other | 1 | 0.0003% |
| Acidaminococcus | Other | 1 | 0.0002% |
| Enhydrobacter | aerosaccus | 1 | 0.0002% |
| Other | Other | 1 | 0.0002% |
| Anaerococcus | Other | 1 | 0.0002% |
| Treponema_2 | parvum | 1 | 0.0001% |

Figure 8:
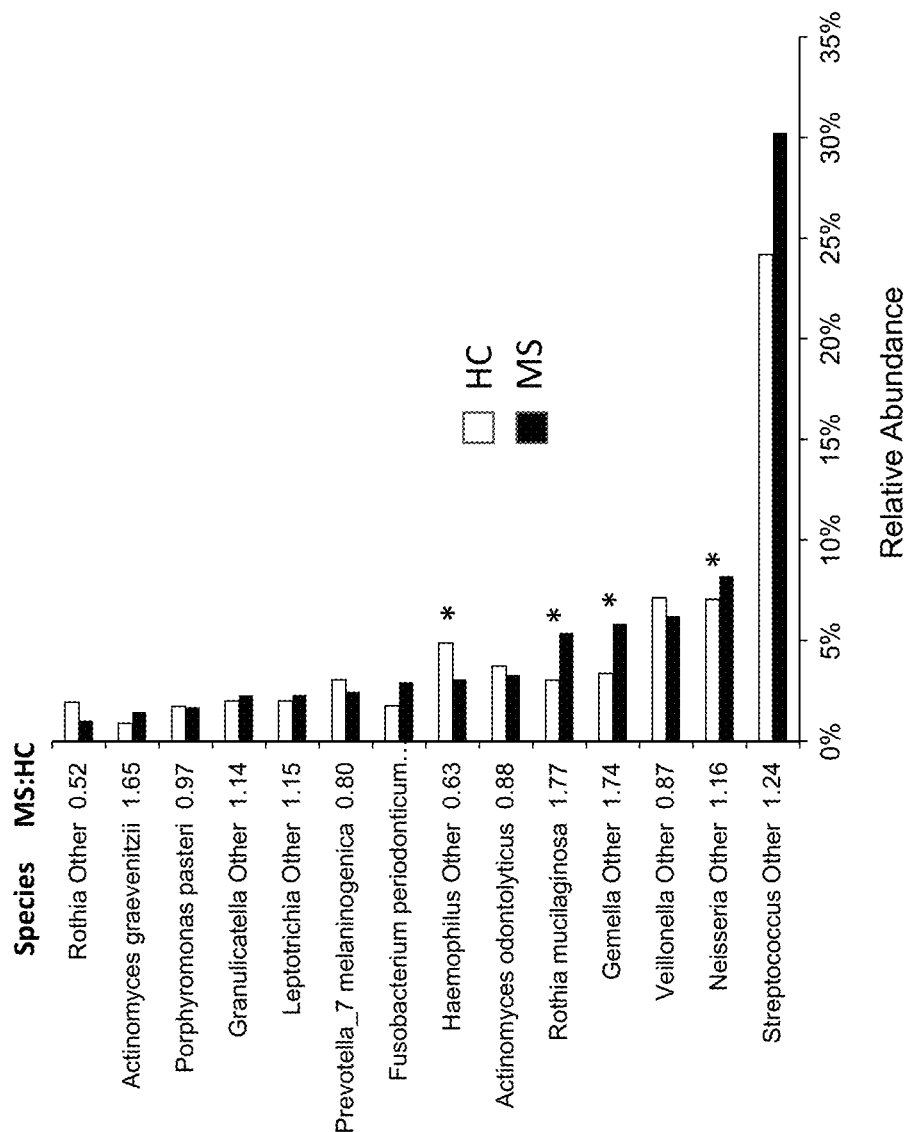
FIG. 8 shows the relative abundance of bacterial species in MS patients and healthy controls (HC) for the species present at 1% or higher. P<0.05, Mann Whitney U test.

Comparison of the MS to HC groups (FIG. 8) shows that 3 species (*Gemella*_other, *Rothia mucilaginosa*, and *Neisseria*_other) were significantly increased in MS patients; while *Heamophilus*_other was significantly decreased in MS samples. ROC curves (FIG. 9) show that *Gemella* other and *Rothia muscilaginoa* were good classifiers with AUC values of 0.757 and 0.747, sensitivity of 83% and 75%, and good specificity. ROC curve of *Haemophilus*_other (FIG. 10) also has a good AUC (0.740), good sensitivity (83%) but poor specificity. Combined ROC curves for these species did not show improvement over individual species. Table 5 shows differences in species between MS patients and healthy controls.

TABLE 5

Examples of species that differ between MS patients and healthy controls.

| Genus | Species | MS ave | HC ave | MS:HC |
|---|---|---|---|---|
| Alloprevotella | Other | 0.956% | 1.910% | 0.50 |
| | rava | 0.045% | 0.117% | 0.39 |
| | tannerae | 0.033% | 0.162% | 0.21 |
| Campylobacter | concisus | 0.567% | 1.046% | 0.54 |
| | curvus | 0.000% | 0.004% | 0.00 |
| | gracilis | 0.028% | 0.066% | 0.43 |
| | Other | 0.372% | 0.485% | 0.77 |
| Haemophilus | haemolyticus | 0.000% | 0.003% | 0.00 |
| | Other | 3.069% | 4.860% | 0.63 |
| Lautropia | mirabilis | 0.298% | 0.741% | 0.40 |
| | Other | 0.061% | 0.697% | 0.09 |
| Prevotella_2 | conceptionensis | 0.020% | 0.048% | 0.42 |
| | marshii | 0.000% | 0.003% | 0.00 |
| | saccharolytica | 0.001% | 0.016% | 0.06 |
| | shahii | 0.066% | 0.116% | 0.57 |
| Gemella | Other | 5.829% | 3.348% | 1.74 |
| Streptococcus | massiliensis | 0.017% | 0.008% | 2.13 |
| | mutans | 0.035% | 0.010% | 3.51 |
| | oralis | 0.062% | 0.000% | >1 |
| | Other | 30.223% | 24.181% | 1.25 |
| Rothia | mucilaginosa | 5.38% | 3.03% | 1.77 |

Figures 11A, 11B:
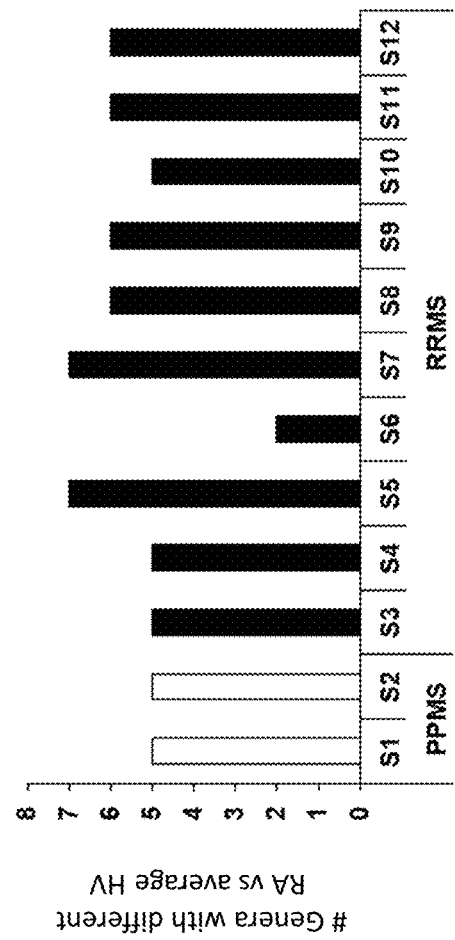
FIGS. 11A-B shows the number of MS patients who show the same change in relative abundance for 7 genera, as was found for the MS group as a whole.

FIG. 11A shows the overall ratio of relative abundance in MS patients (n=12 total) compared to HCs for 7 genera that were found significantly different between the 2 groups; and shows that the ratio for 2 genera (*Gemella* and *Staphylococcus*) is >1; and for the 5 others is <1. *, *Prevotella_2* and *Staphylococcus* were significantly different between RRMS (n=10) and HCs, but not between PPMS and HCs. FIG. 11B shows for each individual MS patient how many of the 7 genera showed the same change (relative to HC) as presented in FIG. 11A. In the RRMS group (filled bars) for subjects S5 and S7, 7 genera showed the same change as in FIG. 11A; for subjects S8, S9, S11, and S12 there were 6 of the 7 genera that were the same; for subjects S3, S4 and S10 there were 5 of the 7 genera that were the same; and for S6 2 of the 7 genera showed the same relative changed as in FIG. 11A. Overall, the 10 RRMS patients showed the same change in relative abundance for 5 or 6 of the 7 genera. For the 2 PPMS patients 51 and S2 (white bars) 5 of the genera showed the same change as shown in FIG. 11A.

What is claimed is:

1. A method of diagnosing and treating multiple sclerosis (MS) in a subject, the method comprising:
    a) obtaining a saliva sample from the subject;
    b) detecting in the saliva sample an increased abundance of a *Gemella*, a *Staphylococcus*, and a *Streptococcus* genus of bacteria and a decreased abundance of a *Haemophilus*, a *Campylobacter*, and a *Prevotella_2* genus of bacteria relative to that of a saliva sample obtained from a control subject, thereby diagnosing MS in the subject; and
    c) administering to the subject diagnosed with MS administering a disease-modifying therapy, wherein the disease-modifying therapy is interferon beta-1a, interferon beta-1b, glatiramer acetate, ofatumumab, peginterferon beta-1a, teriflunomide, monomethyl fumarate, dimethyl fumarate, fingolimod, cladribine, siponimod, diroximel fumarate, ozanimod, alemtuzumab, mitoxantrone, ocrelizumab or natalizumab.

2. The method of claim 1, further comprising administering to the subject diagnosed with MS a salivary microbiome altering agent to support growth of *Haemophilus*, *Campylobacter*, or *Prevotella_2*.

3. The method of claim 1, wherein relative abundance of the *Gemella*, *Staphylococcus*, *Streptococcus*, *Haemophilus*, *Campylobacter*, and *Prevotella_2* genus of bacteria is determined by nucleic acid sequencing.

4. The method of claim 3, wherein the nucleic acid sequencing is determined using 16S rRNA amplicon sequencing.

5. The method of claim 3, wherein the nucleic acid sequencing is determined using quantitative PCR.

6. The method of claim 1, wherein detecting of the increased abundance of the *Gemella*, *Staphylococcus*, and *Streptococcus* genus of bacteria and the decreased abundance of a *Haemophilus*, *Campylobacter*, and *Prevotella_2* genus of bacteria includes at least one assay selected from the group consisting of nucleic acid sequencing, PCR amplification, a competitive binding assay, a non-competitive binding assay, a radioimmunoassay, immunohistochemistry, an enzyme-linked immunosorbent assay (ELISA), a sandwich assay, a gel diffusion immunodiffusion assay, an agglutination assay, dot blotting, a fluorescent immunoassay such as fluorescence-activated cell sorting (FACS), a chemiluminescence immunoassay, an immunoPCR immunoassay, a protein A or protein G immunoassay, and an immunoelectrophoresis assay.

7. The method of claim 1, wherein subject is a human.

8. The method of claim 1, wherein the subject is suspected of having or is at risk of developing MS or a relapse of MS.

* * * * *